US012590386B2

(12) United States Patent
Johnson et al.

(10) Patent No.: US 12,590,386 B2
(45) Date of Patent: Mar. 31, 2026

(54) RECOMBINANT POLYCLONAL PROTEINS AND METHODS OF USE THEREOF

(71) Applicant: GigaGen, Inc., South San Francisco, CA (US)

(72) Inventors: David Scott Johnson, San Francisco, CA (US); Adam Shultz Adler, Belmont, CA (US); Rena Aviva Mizrahi, Pacifica, CA (US); Yoong Wearn Lim, South San Francisco, CA (US); Michael Asensio, South San Francisco, CA (US); Sheila Keating, South San Francisco, CA (US); Renee Leong, Daly City, CA (US); Jackson Leong, San Francisco, CA (US)

(73) Assignee: GigaGen, Inc., San Carlos, CA (US)

( * ) Notice: Subject to any disclaimer, the term of this patent is extended or adjusted under 35 U.S.C. 154(b) by 1092 days.

(21) Appl. No.: 17/607,497

(22) PCT Filed: Apr. 30, 2020

(86) PCT No.: PCT/US2020/030878
§ 371 (c)(1),
(2) Date: Oct. 29, 2021

(87) PCT Pub. No.: WO2020/223573
PCT Pub. Date: Nov. 5, 2020

(65) Prior Publication Data
US 2022/0243197 A1      Aug. 4, 2022

Related U.S. Application Data

(60) Provisional application No. 62/841,097, filed on Apr. 30, 2019.

(51) Int. Cl.
*C40B 40/10* (2006.01)
*C07K 16/00* (2006.01)

(52) U.S. Cl.
CPC .............. *C40B 40/10* (2013.01); *C07K 16/00* (2013.01)

(58) Field of Classification Search
None
See application file for complete search history.

(56) References Cited

U.S. PATENT DOCUMENTS

| | | | |
|---|---|---|---|
| 2004/0009168 A1 | 1/2004 | Kaisheva et al. | |
| 2010/0310558 A1 | 12/2010 | Oleksiewicz et al. | |
| 2018/0258422 A1 | 9/2018 | Gigagen | |

FOREIGN PATENT DOCUMENTS

| | | |
|---|---|---|
| CN | 101395182 A | 3/2009 |
| CN | 101688204 A | 3/2010 |
| CN | 102199593 A | 9/2011 |
| JP | 2007-505611 A | 10/2007 |

(Continued)

OTHER PUBLICATIONS

PCT International Search Report and Written Opinion, International Application No. PCT/US2020/030878, dated Dec. 21, 2020, 11 pages.

(Continued)

*Primary Examiner* — Christian C Boesen
(74) *Attorney, Agent, or Firm* — Fenwick & West LLP

(57) ABSTRACT

Provided herein are compositions comprising recombinant polyclonal proteins (RPPs) derived from mammalian plasma cells and plasmablasts. Also provided are methods of using the RPPs.

6 Claims, 7 Drawing Sheets
Specification includes a Sequence Listing.

c Product region complementary to d
d Product region complementary to c
e Polymerase
g Polynucleic acid target #1
h Polynucleic acid target #2
i Fused product between polynucleic acid targets #1 and #2
j Physical reaction container or emulsion droplet

(56) References Cited

FOREIGN PATENT DOCUMENTS

| JP | 2015-521850 A | 8/2015 |
|---|---|---|
| WO | WO 2004/061104 A2 | 7/2004 |
| WO | WO 2005/042774 A2 | 5/2005 |
| WO | WO 2007/101441 A1 | 9/2007 |
| WO | WO 2008/145133 A2 | 12/2008 |
| WO | WO 2009/030237 A2 | 3/2009 |
| WO | WO 2014/005042 A2 | 1/2014 |
| WO | WO 2016/200577 A1 | 12/2016 |
| WO | WO 2018/170013 A1 | 9/2018 |
| WO | WO 2020/223573 A2 | 11/2020 |
| WO | WO 2021/253002 A1 | 12/2021 |
| WO | WO 2022/031834 A1 | 2/2022 |

OTHER PUBLICATIONS

Adler et al., "Rare, high-affinity anti-pathogen antibodies from human repertoires, discovered using microfluidics and molecular genomics," MAbs, Aug. 28, 2017, vol. 9, Iss. 8, pp. 1282-1296, entire document.

Ferrara et al., "Recombinant renewable polyclonal antibodies," MAbs, Dec. 20, 2014, vol. 7, Iss. 1, pp. 32-41, entire document.

Reason et al., "Human Fab Fragments Specific for the Haemophilus influenzae b Polysaccharide Isolated from a Bacteriophage Combinatorial Library Use Variable Region Gene Combinations and Express an Idiotype That Mirrors in Vivo Expression," Infection and Immunity, Jan. 1, 1997, vol. 65, No. 1, pp. 261-266, entire document.

Bendig, M.M., "Humanization of Rodent Monoclonal Antibodies by CDR Grafting," Methods: A Companion to Methods in Enzymology, 1995; 8:83-93.

Bloch et al., "Deployment of convalescent plasma for the prevention and treatment of COVID-19," The Journal of Clinical Investigation, vol. 130, No. 6, Jun. 1, 2020 (Jun. 1, 2020), pp. 2757-2765, XP055815868, GB ISSN: 0021-9738, DOI: 10.1172/JCI138745.

Branche, E. et al., "Human Polyclonal Antibodies Prevent Lethal Zika Virus Infection in Mice", Scientific Reports, vol. 9, Article No. 9857, Jul. 8, 2019 (Jul. 8, 2019), pp. 1-12, XP055664845.

Colman. P.M., "Effects of amino acid sequence changes on antibody-antigen interactions," Research in Immunology, 1994, 145:33-36.

Cross, "Searching for a coronavirus cure in the blood," Chemical & Engineering New, Apr. 7, 2020 (Apr. 7, 2020), XP055850922, 7 pages, Retrieved from the Internet: URL:https://cen.acs.org/pharmaceuticals/biologics/Searching-coronavirus-cure-blood/98/i14 [retrieved on Oct. 13, 2021].

Frandsen, T.P. et al., "Consistent manufacturing and quality control of a highly complex recombinant polyclonal antibody product for human therapeutic use", Biotechnology and Bioengineering, vol. 108, Issue 9, Sep. 2011, pp. 2171-2181, XP071108999.

Gigagen Press Release, "COVID-19 Antibody Therapy: GigaGen Initiates Development of rCIG," Outbreak News Today, Mar. 30, 2020 (Mar. 30, 2020), 4 pages, XP055850665, Retrieved from the Internet: URL:http://outbreaknewstoday.com/covid-19-antibody-therapy-gigagen-initiates-development-of-rcig-21518/ [retrieved on Oct. 12, 2021].

Goldstein et al., "Massively parallel single-cell B-cell receptor sequencing enables rapid discovery of diverse antigen-reactive antibodies," Communications Biology, vol. 2, Article No. 304, Aug. 9, 2019 (Aug. 9, 2019), pp. 1-10, XP055758874, DOI: 10.1038/s42003-019-0551-y.

Hammarström et al., "Development of passive immunity against SARS-CoV-2 for management of immunodeficient patients-a perspective," Journal of Allergy and Clinical Immunology, Elsevier, Amsterdam, NL, vol. 146, No. 1, May 12, 2020 (May 12, 2020), pp. 58-60, P086207336, ISSN: 0091-6749, DOI: 10.1016/J.JACI.2020.04.043 [retrieved on May 12, 2020].

International Preliminary Report on Patentability, Patent Cooperation Treaty Application No. PCT/US2020/030878, Nov. 2, 2021, 8 pages.

International Search Report and Written Opinion, Patent Cooperation Treaty Application No. PCT/US2021/037232, Nov. 8, 2021, 16 pages.

International Search Report and Written Opinion, Patent Cooperation Treaty Application No. PCT/US2021/044523, Nov. 18, 2021, 19 pages.

Keating, S.M. et al., "Capturing and Recreating Diverse Antibody Repertoires as Multivalent Recombinant Polyclonal Antibody Drugs," bioRxiv, preprint, Aug. 6, 2020, 78 pages.

Keating, S.M. et al., "Generation of recombinant hyperimmune globulins from diverse B-cell repertoires," nature biotechnology, vol. 39, No. 8, Aug. 2021, pp. 989-999, XP037534475.

Khantasup, K. et al., "Design and Generation of Humanized Single-chain Fv Derived from Mouse Hybridoma for Potential Targeting Application," Monoclonal Antibodies in Immunodiagnosis and Immunotherapy, 2015, 34(6): 404-417.

Lou, Y. et al., "Cross-neutralization antibodies against SARS-CoV-2 and RBD mutations from convalescent patient antibody libraries," bioRxiv, posted on Jun. 6, 2020, 32 pages.

Murphy, C. et al., "Enhancing recombinant antibody performance by optimally engineering its format," Journal of Immunological Methods, vol. 463, Dec. 2018, pp. 127-133.

Non-final Office Action, U.S. Appl. No. 17/386,504, filed Mar. 2, 2022, 27 pages.

Paul, W.E. (ed), Fundamental Immunology, 3rd Edition, Chapter 9, Structure and Function of Immunoglobulins, 1993, pp. 292-295.

Ravichandran, S. et al., Antibody repertoire induced by SARS-CoV-2 spike protein immunogens, bioRxiv, posted on May 13, 2020, 34 pages.

Rudikoff, S. et al., "Single amino acid substitution altering antigen-binding specificity," Proc. Natl. Acad. Sci. USA, 1982, 79(6):1979-1983.

Shen et al., "Treatment of 5 Critically Ill Patients With COVID-19 With Convalescent Plasma," JAMA the Journal of the American Medical Association, vol. 323, No. 16, Mar. 27, 2020 (Mar. 27, 2020), p. 1582-1589, XP055725009, US ISSN: 0098-7484, DOI: 10.1001/jama.2020.4783.

Sheridan, "Convalescent serum lines up as first-choice treatment for coronavirus," Nature Biotechnology, Gale Group Inc, New York, vol. 38, No. 6, May 1, 2020 (May 1, 2020), pp. 655-658, XP037167671, ISSN: 1087-0156, DOI: 10.1038/D41587-020-00011-1 [retrieved on May 1, 2020].

Tanno et al. "A facile technology for the high-throughput sequencing of the paired VH:VL and TCRβ:TCRα repertoires," Science Advances, Apr. 22, 2020, vol. 6, Issue 17, 8 pages, XP55851688, Retrieved from the Internet: URL:https://www.science.org/doi/pdf/10.1126/sciadv.aay9093 [retrieved on Oct. 15, 2021].

Tiberghien et al., "Collecting and evaluating convalescent plasma for COVID-19 treatment: why and how?", Vox Sanguinis, vol. 115, No. 6, May 3, 2020 (May 3, 2020), pp. 488-494, XP055815870, Ch ISSN: 0042-9007, DOI: 10.1111/vox.12926.

World Health Organization, "Landscape analysis of therapeutics as Feb. 17, 2020," Feb. 25, 2020 (Feb. 25, 2020), XP055809736, Retrieved from the Internet: URL:https://web.archive.org/web/20200225223659/https://www.who.int/blueprint/priority-diseases/key-action/Table_of_therapeutics_Appendix_17022020.pdf?ua=1, pp. 26,28.

Yuan, A.Q. et al., Isolation of and Characterization of Neutralizing Antibodies to Covid-19 from a Large Human Naïve scFv Phage Display Library, bioRxiv, posted on May 19, 2020, 15 pages.

Chi, X., et al., "A neutralizing human antibody binds to the N-terminal domain of the Spike protein of SARS-CoV-2," Science, Jun. 22, 2020, vol. 369, Issue 6504, pp. 650-655.

Partial Supplementary European Search Report, European Patent Application No. 20799387.7, Jan. 4, 2023, 12 pages.

United States Office Action, U.S. Appl. No. 17/386,504, filed Dec. 7, 2022, 22 pages.

United States Office Action, U.S. Appl. No. 17/469,493, filed Dec. 30, 2022, 11 pages.

Wang, B., et al., "Functional Interrogation and Mining of Natively-Paired Human VH:VL Antibody Repertoires," Nature Biotechnology, author manuscript, Feb. 2018; 36(2): 152-155, 14 pages.

(56) References Cited

OTHER PUBLICATIONS

Wang, Q., et al., "Molecular determinants of human neutralizing antibodies isolated from a patient infected with Zika virus," Science Translational Medicine, Dec. 14, 2016, vol. 8, issue 369, 10 pages.

Berger, M., "Antibodies to vaccine antigens in pooled polyclonal human IgG products," TRANSFUSION, vol. 58, No. S3, Dec. 2018, pp. 3096-3105.

Chao, R. et al., Recent advances in DNA assembly technologies, Jan. 6, 2015, FEMS Yeast Res., 15/a, pp. 1-9.

Dekosky, B.J. et al., "High-throughput sequencing of the paired human immunoglobulin heavy and light chain repertoire," Nature Biotechnology, vol. 31, No. 2, Feb. 2013, pp. 166-169, Online Methods.

European Patent Office, Extended European Search Report and Opinion, EP Patent Application No. 23192977.9, Feb. 5, 2024, eight pages.

Extended European Search Report, European Patent Application No. 20799376.7, Apr. 6, 2023, 8 pages.

Lai, J.C.Y. et al., "CD45 Regulates Migration, Proliferation, and Progression of Double Negative 1 Thymocytes," The Journal of Immunology, vol. 185, No. 4, Aug. 15, 2010, pp. 2059-2070.

Mourad, G. et al., "The role of Thymoglobulin induction in kidney transplantation: an update," Clinical Transplantation, vol. 26, No. 5, Oct. 14, 2012, pp. E450-E464.

Ramisse, F. et al., "Passive and Active Immunotherapy for Experimental Pneumococcal Pneumonia by Polyvalent Human Immunoglobulin or F(ab')2 Fragments Administered Intranasally," The Journal of Infectious Diseases, vol. 173, Jan. 27, 1995, pp. 1123-1128.

Rinaldi, C. et al., "Modulation of Innate Immune Responses by Influenza-Specific Ovine Polyclonal Antibodies Used for Prophylaxis," Plos One, vol. 9, No. 2, Feb. 28, 2014, e89674, pp. 1-9.

Rothstein, S.S. et al., "Passive immunization for hepatitis B," Journal of Oral and Maxillofacial Surgery, vol. 40, No. 1, Jan. 1, 1982, pp. 34-37.

Slifka, M.K. et al., "Passive Immunization—an 1-13 overview: Science Direct Topics," Apr. 19, 2016, pp. 1-9.

Todd, S.C. et al., "Brief Definitive 2 Report: CD81 Expressed on Human Thymocytes Mediates Integrin Activation and Interleukin 2-dependent Proliferation," J. Exp. Med., vol. 184, Nov. 1996, pp. 2055-2060.

g Polynucleic acid target #1
h Polynucleic acid target #2
i Solid support, such as a bead
j Physical reaction container or emulsion droplet
k Plasmablast or plasma cell a Left primer for target #1
b Right primer for target #1
c Primer region complementary to d
d Primer region complementary to c
e Left primer for target #2
f Right primer for target #2
g Polynucleic acid target #1
h Polynucleic acid target #2
i Solid support, such as a bead
j Physical reaction container or emulsion droplet a Left primer for target #1
b Right primer for target #1
c Primer region complementary to d
d Primer region complementary to c
e Left primer for target #2
f Right primer for target #2
g Polynucleic acid target #1
h Polynucleic acid target #2
j Physical reaction container or emulsion droplet c Product region complementary to d
d Product region complementary to c
g Polynucleic acid target #1
h Polynucleic acid target #2
j Physical reaction container or emulsion droplet c Product region complementary to d
d Product region complementary to c
e Polymerase
g Polynucleic acid target #1
h Polynucleic acid target #2
i Fused product between polynucleic acid targets #1 and #2
j Physical reaction container or emulsion droplet

RECOMBINANT POLYCLONAL PROTEINS AND METHODS OF USE THEREOF

1. CROSS REFERENCE TO RELATED APPLICATIONS

This present application is a 35 U.S.C. 371 Patent Application of PCT Application No. PCT/US2020/030878, filed Apr. 30, 2020, which claims the benefit of and priority to U.S. Provisional Application No. 62/841,097 filed on Apr. 30, 2019, the contents of which are incorporated by reference in their entirety for all purposes.

2. SEQUENCE LISTING

The instant application contains a Sequence Listing with 120158 sequences which has been submitted via EFS-Web and is hereby incorporated by reference in its entirety. Said ASCII copy, created on Apr. 30, 2020, is named GGN035WOsequencelisting.txt, and is 30.3 MB in size.

3. FIELD

Provided herein are recombinant polyclonal proteins (RPPs), also called recombinant polyclonal antibody proteins, recombinant hyperimmune globulins, or simply recombinant hyperimmunes, with binding specificity for antigens comprising, e.g., vaccines and libraries and compositions comprising such RPPs, including pharmaceutical compositions. Also provided are methods of making RPPs, and methods of using RPPs, for example, for therapeutic purposes.

4. BACKGROUND

Widespread use of active vaccines has greatly reduced the incidence of preventable infectious diseases, but vaccine failure due to low or no vaccine-induced immune response remains a significant problem. Certain populations are especially at risk of infection, including the elderly or individuals with congenital humoral immune deficiencies; their weakened immune systems prevent induction of adequate immune responses to vaccine antigens. (D'Acremont et al., 2006; Jilkovi et al., 2009; Weinberger et al., 2010; Langley et al., 2011; Cramer et al., 2016; Bader, 2007; Goldacker et al., 2007; van Assen et al., 2010). Poor responders suffer from a significantly elevated risk of infection, leading to increased rates hospitalization, requiring antibiotic or antiviral therapy, or causing long-term illness or death. These patients would benefit from antibody replacement therapies that would provide protective immunity as an alternative to failed vaccine modalities.

Passive immunizations (McDonagh, 1966) offer alternative protective strategies for immunodeficient individuals who do not respond to active vaccines. For example, intravenous immunoglobulin (IVIg) is a broad-spectrum polyclonal antibody therapy derived from the plasma of thousands of human donors. IVIg is used as an antibody replacement therapy for patients with humoral immune deficiencies (Lucas et al., 2010; Resnick et al., 2012). However, IVIg has a low titer of antibodies directed against many common pathogens, which leads to significant morbidity and mortality in immune deficient patients (Orange et al., 2010). To increase anti-pathogen titers, some groups have developed high-titer plasma-derived antibodies, often called hyperimmunes (Bozzo & Jorquera, 2017). Hyperimmunes are commonly derived from the plasma of donors soon after administration of active vaccines, such as Hyper-HEP B (Grifols), which has a high titer against Hepatitis B virus.

Hyperimmunes derived from donors recently administered active vaccines are excellent choices for passive immunization, but to scale such products commercially is a challenge (Kreil et al., 2012). Importantly, it can be difficult to identify strong responders who are willing to be vaccinated and donate plasma repeatedly. Therefore, hyperimmune manufacturing lots are necessarily derived from different sets of donors, resulting in lot-to-lot variability. The anti-pathogen titer varies significantly across hyperimmunes, from as low as 2- to 3-fold (Schampera et al., 2017) to as much as 50-fold (Kreil et al., 2012). In some cases, therefore, physicians may simply administer larger doses of IVIg (Polilli et al., 2012). Physicians and patients would benefit from more consistent, higher titer hyperimmunes that are easier to manufacture at large scale.

5. SUMMARY

Provided herein are novel libraries of RPPs (recombinant polyclonal proteins, also called recombinant polyclonal antibody proteins, recombinant hyperimmune globulins, or recombinant hyperimmunes) with binding specificity for antigens comprising, e.g., vaccines, and methods of using such RPPs, e.g., as human therapeutics. The RPPs are recombinant, and their sequences are derived from peripheral blood plasma cells or plasmablasts. The peripheral blood plasma cells or plasmablasts are mobilized by, e.g., a vaccine administered to a donor, and the peripheral blood plasma cells or plasmablasts are specifically separated from other peripheral blood cells. The peripheral blood cells can come from any mammal, for example a mouse, a rat, a human, a monkey, a horse, or a cow.

The RPPs specifically bind antigens. Examples include but are not limited to, a *Haemophilius influenzae* b polysaccharide, a Pneumococcus polysaccharide, a Hepatitis B virus antigen, or a human thymocyte. Some RPP compositions are derived from plasma cells or plasmablasts mobilized by, e.g., vaccines comprising protein antigens derived from viruses. In some embodiments, the vaccine is a mammalian cell, for example an immune cell or a cancer cell. In other embodiments, the vaccine is a killed or inactivated pathogen, for example, a bacterium or a virus. In other embodiments, the vaccine is a bacterial polysaccharide. In some embodiments, the vaccine is an agent cleared by the US Food and Drug Adminstration for prophylaxis against an infectious disease. In all embodiments, the vaccine mobilizes plasma cells or plasmablasts in the peripheral blood, or causes plasma cells or plasmablasts to be mobilized in the peripheral blood.

A library of RPPs comprises a mixture of RPPs, e.g., antibodies, and can be termed a polyclonal antibody. The mixture of antibodies can comprise 10, 100, 1,000, 10,000, 100,000 or more than 100,000 distinct antibody sequences. In some embodiments, the library includes RPPs having the cognate heavy chain CDR3 and light chain CDR3 sequence disclosed herein.

In some embodiments, the antibodies are chimeric. In some embodiments, the antibodies are humanized. In some embodiments, the antibodies are human. In some embodiments, the RPP comprises a mixture of antibody fragments. In some embodiments, the RPPs comprises a mixture of single-chain variable fragments (scFvs). In some embodiments the RPPs comprise full length antibodies. In some embodiments, the antibodies are IgGs, IgAs, or IgMs.

The RPPs provided herein can induce various biological effects associated with binding to an antigen that comprises a vaccine. In some embodiments, an RPP provided herein prevents binding of a virus to a cell, which therein prevents entry of the virus into the cell. In some embodiments, an RPP provided binds to the cell surface of a bacterium, which enables lysis of the bacterium by an immune system. In some embodiments, the RPP binds to the cell surface of a patient's cells, in order to eliminate cells associated with a pathology. In some embodiments, the RPP binds to the surface of T cells, in order to eliminate T cells associated with autoimmune disease or graft-versus-host disease in transplant.

Also provided are isolated polynucleotides encoding the RPPs provided herein, and portions thereof. In some aspects, the present invention provides a mixture of polynucleotides encoding the RPPs provided herein. In other aspects, the present invention provides a mixture of vectors comprising the isolated polynucleotides. In other aspects, the present invention provides a mixture of host cell clones comprising the mixture of polynucleotides or vectors.

Also provided are methods of producing the RPP using the polynucleotides, vectors, or host cells provided herein. Some aspects of the present invention are related to a method of producing RPPs, comprising: expressing the antibodies in host cells using a library of polynucleotide vectors, and isolating the RPP.

Also provided are pharmaceutical compositions comprising the RPPs and a pharmaceutically acceptable excipient.

Also provided are methods of using the RPPs provided herein, e.g., methods of treating or preventing a disease or condition in a subject in need thereof, comprising administering to the subject an effective amount of an RPP provided herein, or a pharmaceutical composition comprising such RPP. In some aspects, the disease or condition is a cancer or Alzheimer's disease. In some aspects, the disease or condition is a viral or bacterial infection. In some aspects the method further comprises administering one or more additional therapeutic agents. In some aspects, the additional therapeutic agent is an immune stimulatory or suppressive agent. In some aspects, the RPP is used to modulate graft-versus-host or host-versus-graft response in a transplantation setting. In some aspects, the RPP is used to moedulate viral disease in a transplantation setting.

In some embodiments, the RPP is in an amount sufficient as prophylaxis against infectious disease when administered to a subject. In some embodiments, the RPP is an amount sufficient to clear infectious disease in an individual actively fighting infection.

In yet a further aspect, the present invention provides for a method for generating a library of recombinant antibodies, comprising: injecting a mammalian donor with an antigen for Hepatitis B Virus (HBV); isolating the donor's plasma cells or plasmablasts; generating the library of recombinant antibodies from the plasma cells or plasmablasts; wherein an activity of the library of recombinant antibodies exceeds a serum titer activity of said donor against the antigen by at least tenfold. The mammalian donor may comprise more than one individual. In one embodiment, the mammalian donor may be a human, mouse, humanized mouse, rat, humanized rat, horse, or cow. The method of the present invention may generate at least 100 recombinant antibodies, for example at least 1,000 recombinant antibodies, such as at least 10,000 recombinant antibodies. In one embodiment, the method of the present invention may generate at least 100,000 recombinant antibodies.

With reference to the method of the present invention, the activity titer may be measured by an in vitro pathogen neutralization assay. Alternatively, the activity titer may be measured by an in vitro binding to antigen assay. In on embodiment, the activity titer may be measured by an in vivo efficacy assay.

In one embodiment, the method of the present invention may further comprise the steps of: obtaining a plurality of first linear polynucleotides, each comprising a first sequence encoding a heavy chain variable domain from a cognate pair from the single plasma cell or plasmablast; and a second sequence encoding a light chain variable domain from the cognate pair; and a third sequence linking the first and second sequences and comprising a restriction site; and obtaining a second linear polynucleotide, not operationally linked to the first polynucleotide, comprising a fourth sequence homologous to a portion of the first polynucleotide; and circularizing each of the plurality of first polynucleotides with the second polynucleotide to generate a library of polynucleotides encoding the library of recombinant antibodies, wherein circularization is effected through Gibson Assembly; and expressing the library of recombinant antibodies in mammalian cells comprising the library of polynucleotides encoding the recombinant antibodies, thereby generating the library of recombinant antibodies.

6. BRIEF DESCRIPTION OF THE DRAWINGS

FIG. 1 summarizes the method of generating libraries of polynucelotides derived from transcripts expressed in peripheral blood plasma cells or plasmablasts isolated from mammalian hosts administered a vaccine.

FIG. 2 summarizes a method of encapsulating plasma cells or plasmablasts into physical containers with lysis mix and solid supports that capture nucleic acid targets from lysed cells.

FIG. 3 summarizes a method of encapsulating target-specific primers with nucleic acid targets affixed to solid supports.

Figure 1:
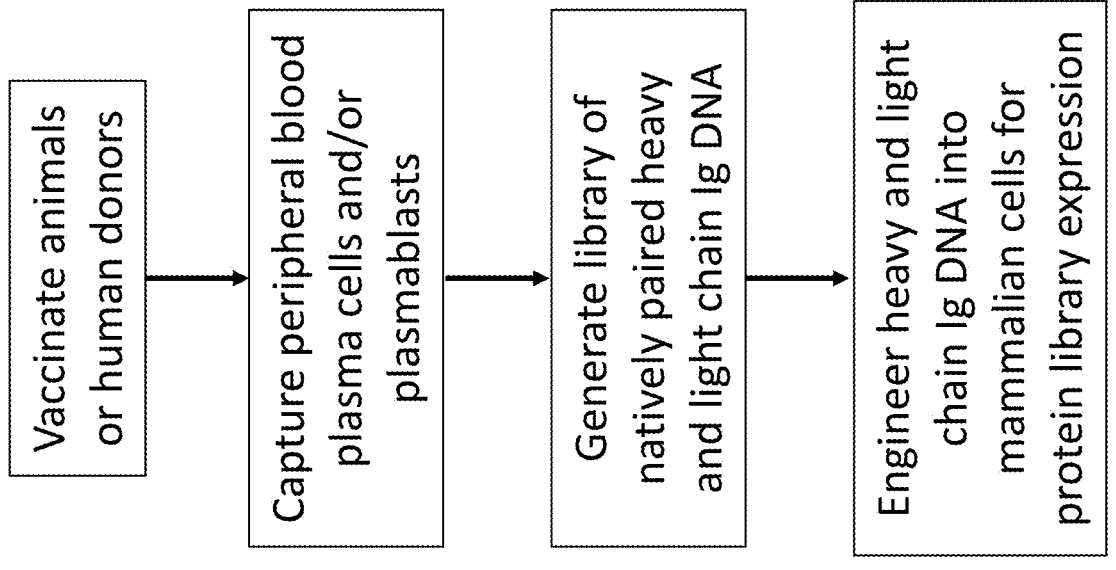
Figure 2:
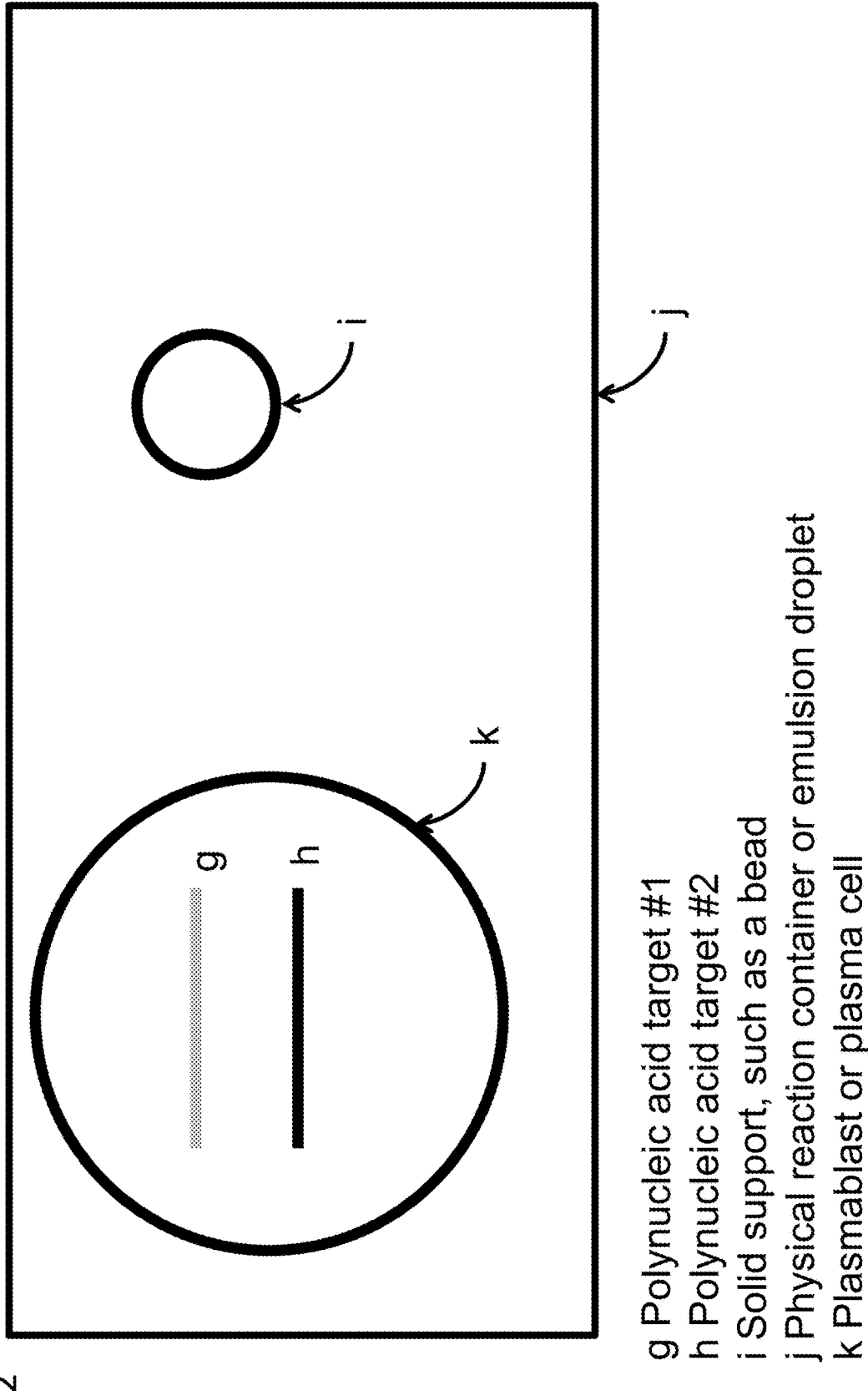
Figure 3:
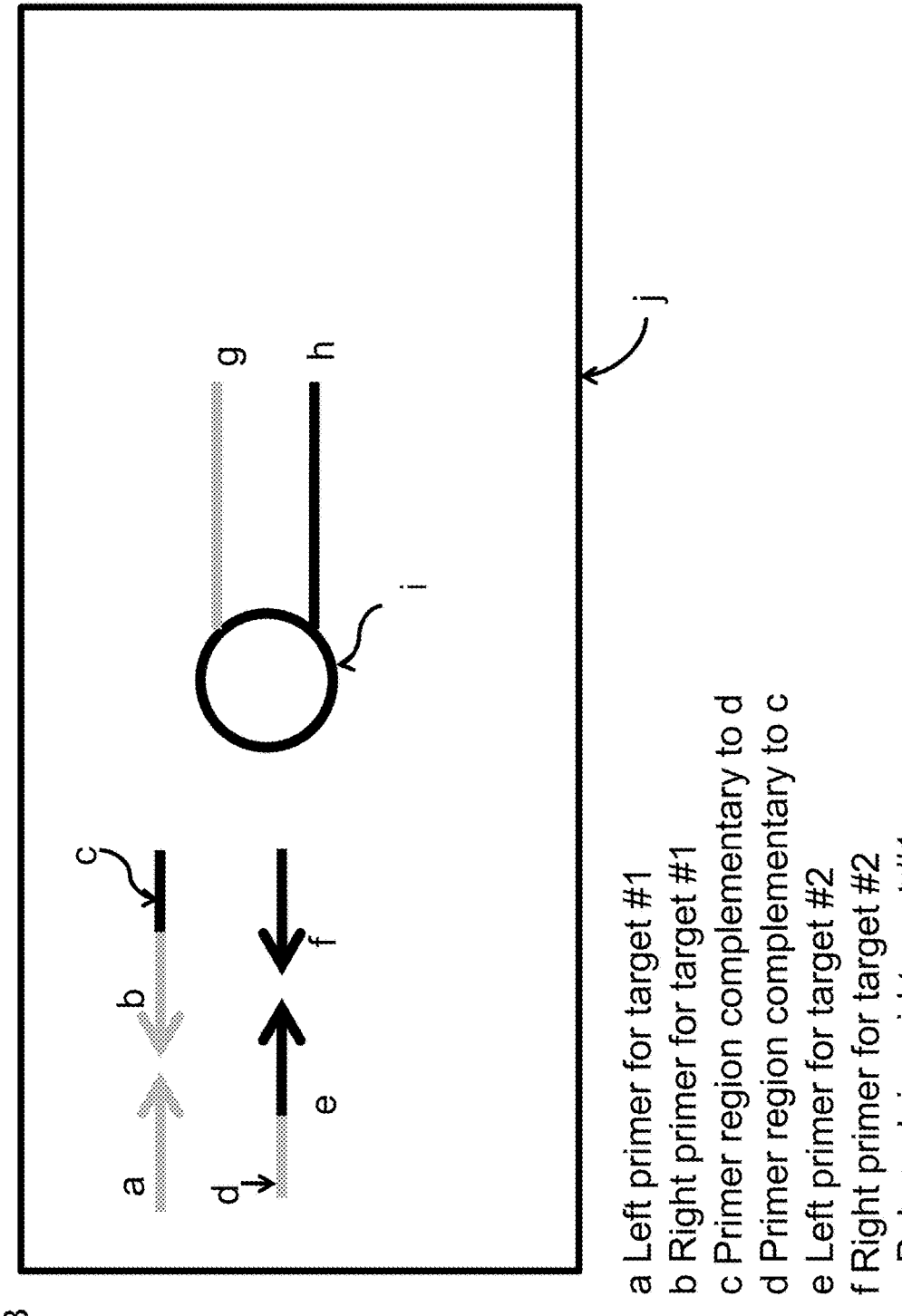
Figure 4:
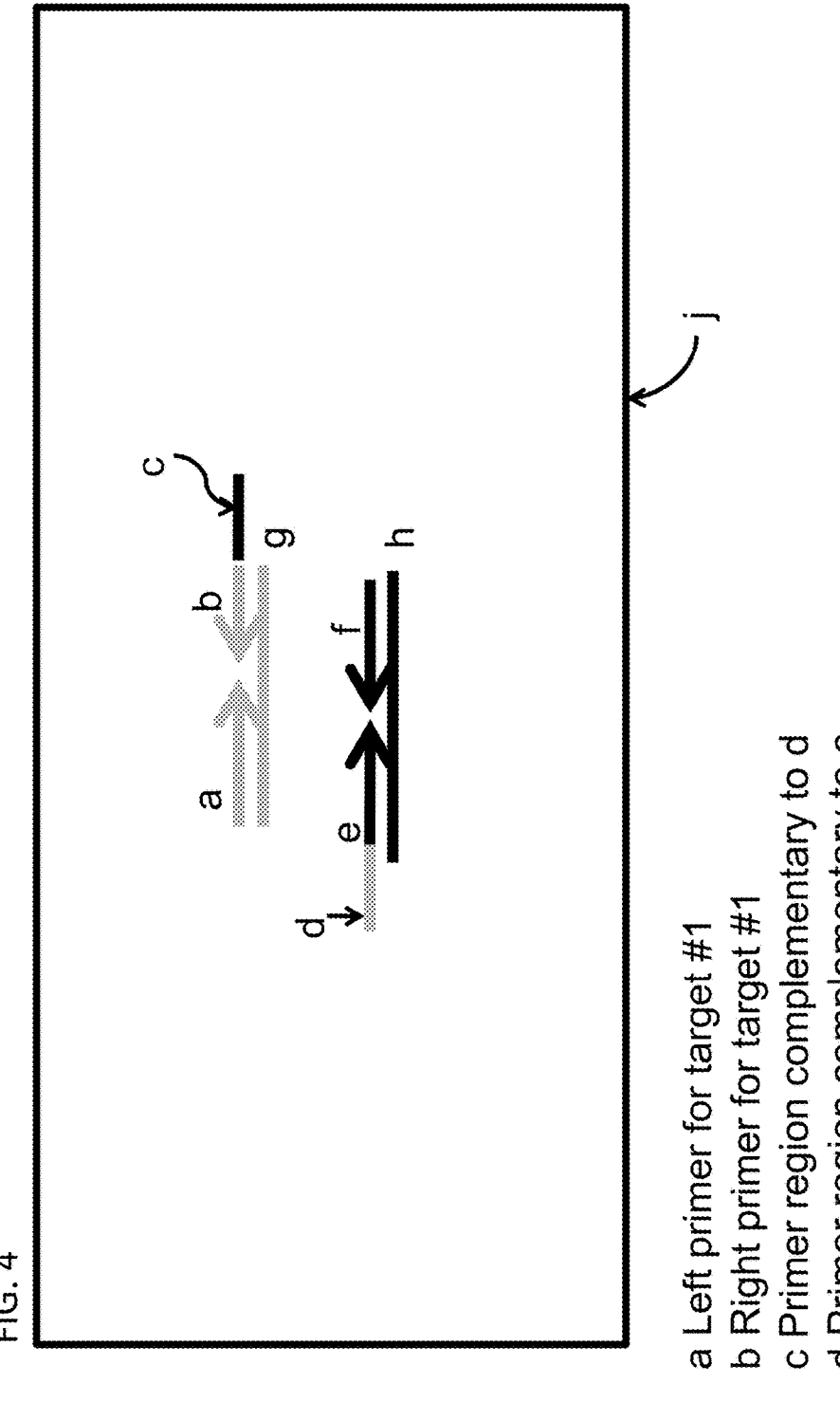
FIG. 4 shows the method of amplifying individual target nucleic acids with complementary regions.
Figure 5:
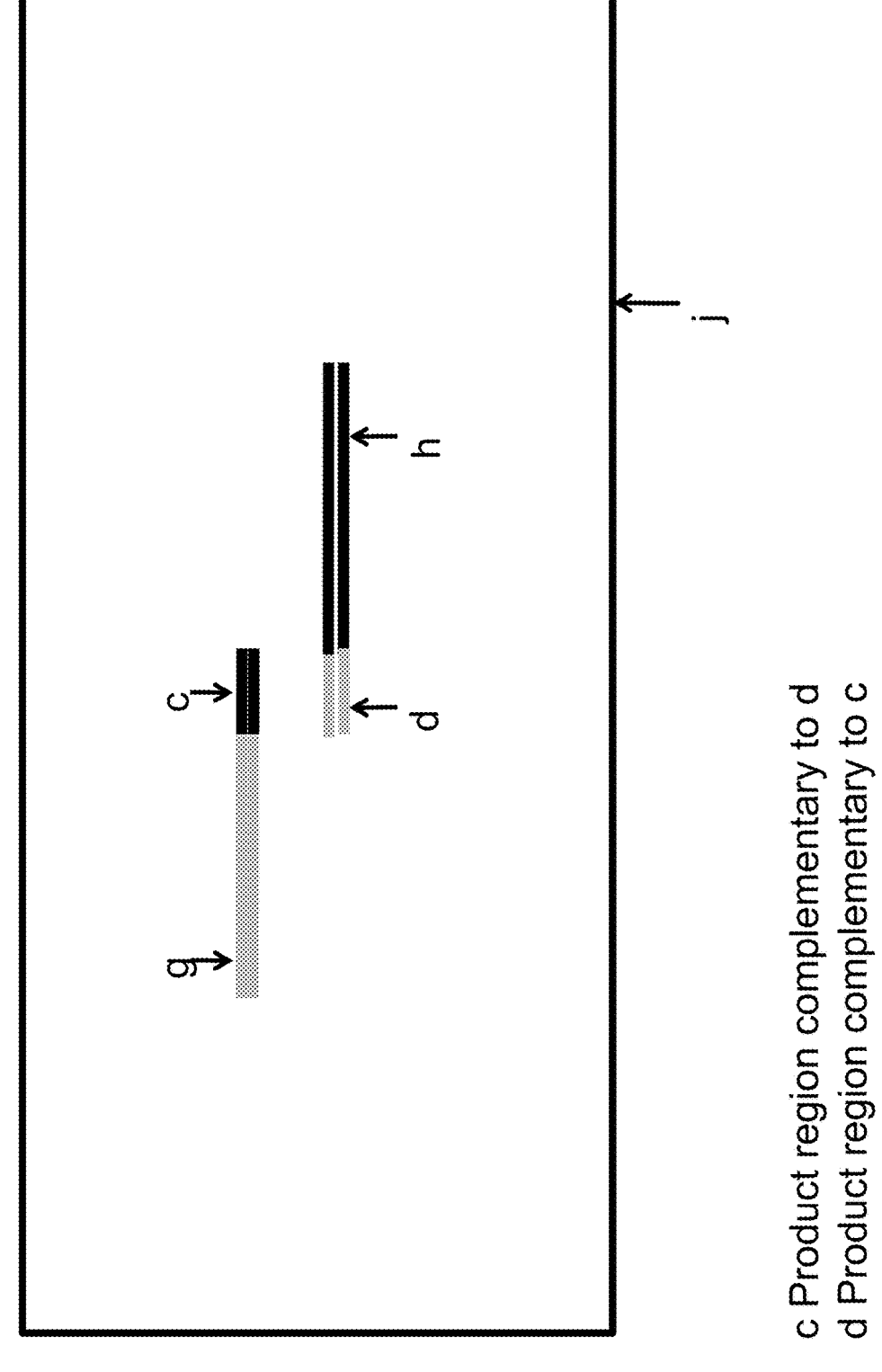
FIG. 5 shows the individual amplified target nucleic acids with complementary regions.
Figure 6:
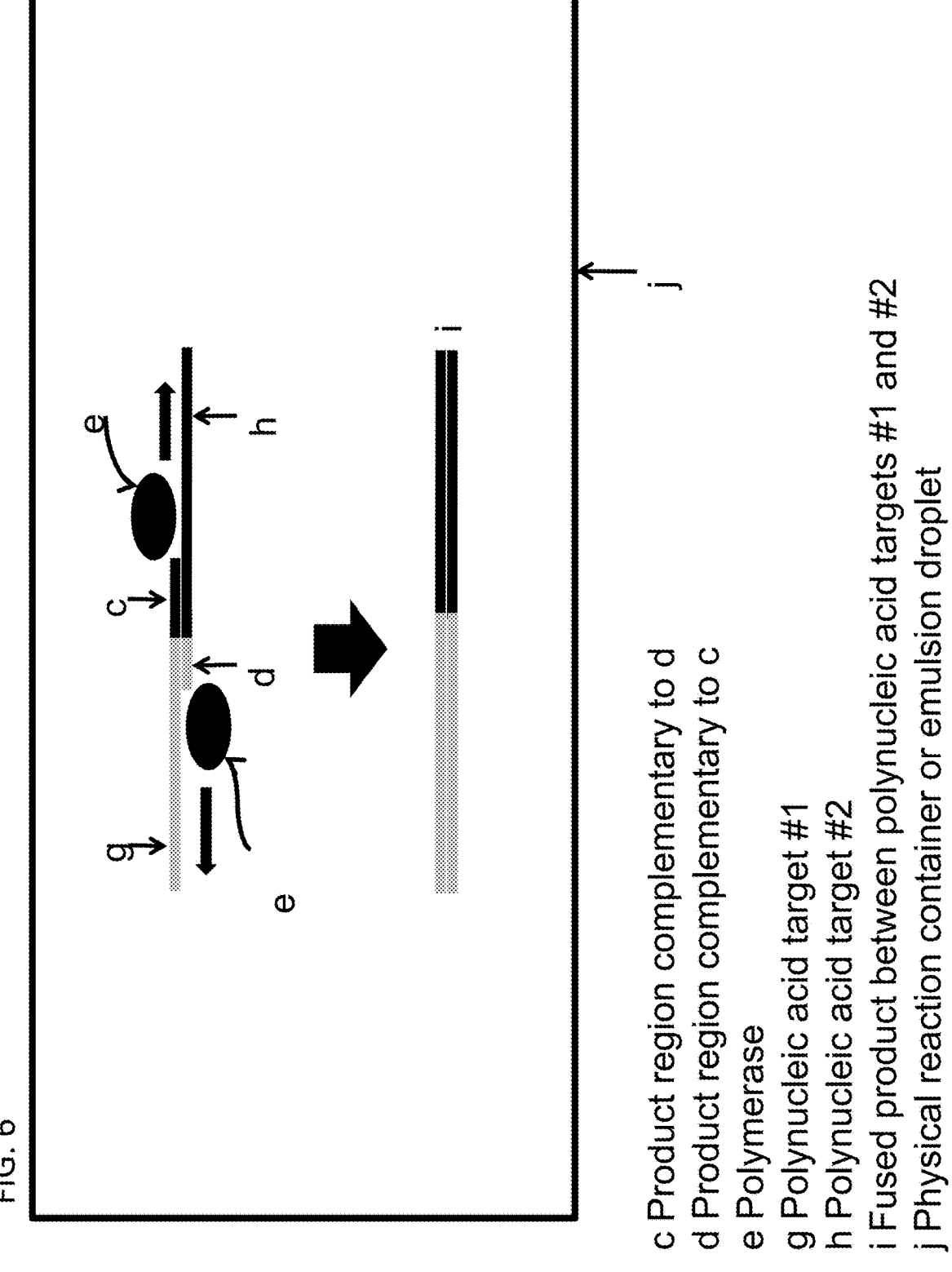

FIG. 6 summarizes a method of fusing separate amplified nucleic acid targets into single fused nucleic acid constructs.

Figure 7:
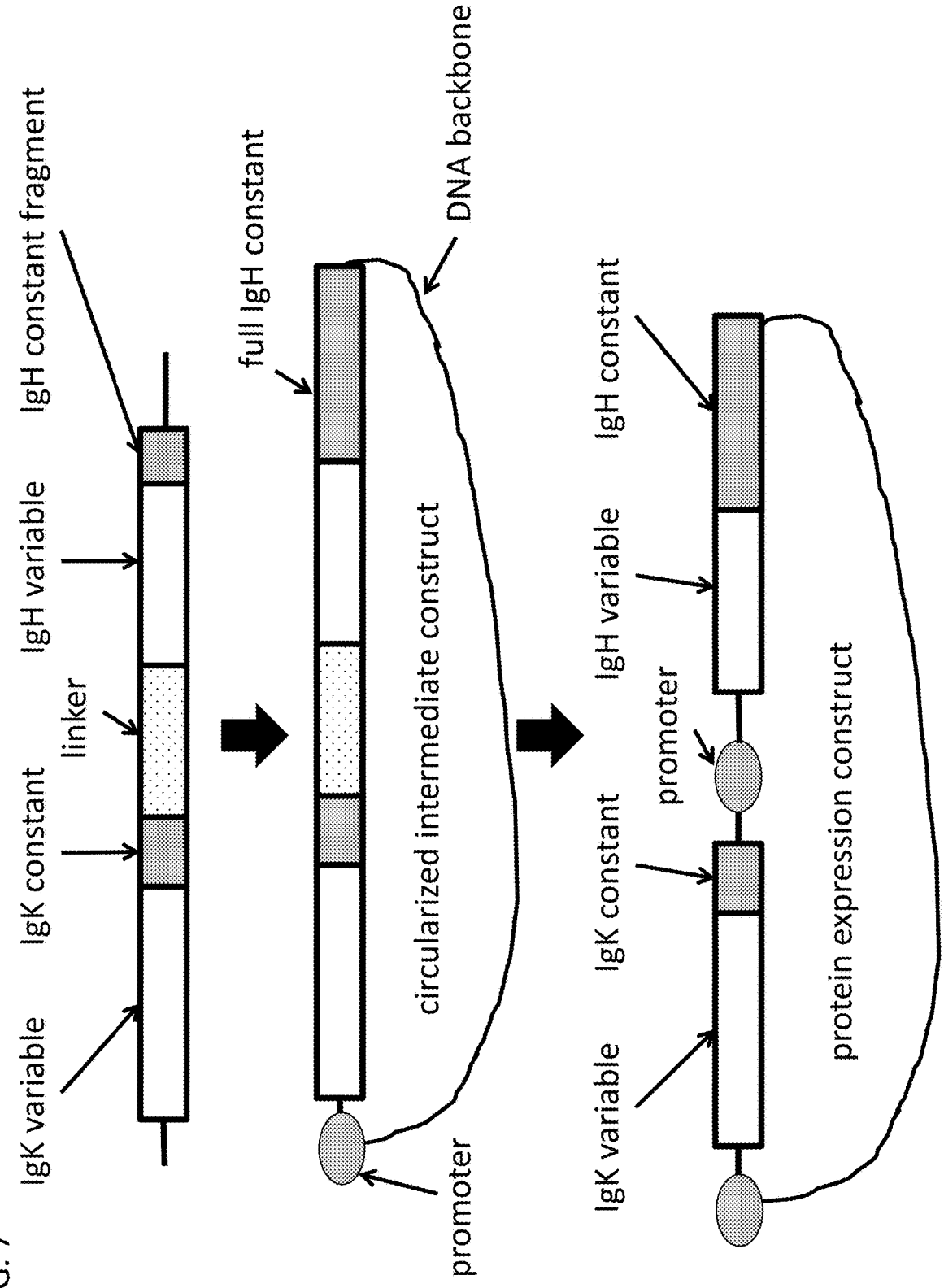

FIG. 7 shows the method of generating circularized gene expression constructs from the fused nucleic acid constructs.

7. DETAILED DESCRIPTION

7.1. Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual, 2d ed.*, Cold Spring Harbor Laboratory Press, Cold Spring Harbor, N.Y. (1989) and Ausubel et al., *Current Protocols in Molecular Biology*, Greene Publishing Associates (1992), and Harlow and Lane *Antibodies: A Laboratory Manual* Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings:

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, PA. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "recombinant polyclonal protein" (RPP) refers to a protein comprising more than one antigen-binding domains that specifically bind to an antigen or epitope, or multiple antigens and epitopes. In some embodiments, the antigen-binding domains bind an antigen or epitope with specificity and affinity similar to that of naturally occurring antibodies. In some embodiments, the RPP comprises antibodies. In some embodiments, the RPP consists of antibodies. In some embodiments, the RPP consists essentially of antibodies. In some embodiments, the RPP comprises alternative scaffolds. In some embodiments, the RPP consists of alternative scaffolds. In some embodiments, the RPP consists essentially of alternative scaffolds. In some embodiments, the RPP comprises antibody fragments. In some embodiments, the RPP consists of antibody fragments. In some embodiments, the RPP consists essentially of antibody fragments.

The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies. One example of an antigen-binding domain is an antigen-binding domain formed by a $V_H$-$V_L$ dimer. Antibodies comprise one type of RPP.

The term "alternative scaffold" refers to a molecule in which one or more regions may be diversified to produce one or more antigen-binding domains that specifically bind to an antigen or epitope. In some embodiments, the antigen-binding domain binds the antigen or epitope with specificity and affinity similar to that of naturally occurring antibodies.

Exemplary alternative scaffolds include those derived from fibronectin (e.g., Adnectins™), the β-sandwich (e.g., iMab), lipocalin (e.g., Anticalins®), EETI-II/AGRP, BPTI/LACI-D1/ITI-D2 (e.g., Kunitz domains), thioredoxin peptide aptamers, protein A (e.g., Affibody®), ankyrin repeats (e.g., DARPins), gamma-B-crystallin/ubiquitin (e.g., Affilins), $CTLD_3$ (e.g., Tetranectins), Fynomers, and (LDLR-A module) (e.g., Avimers). Additional information on alternative scaffolds is provided in Binz et al., *Nat. Biotechnol.*, 2005 23:1257-1268; Skerra, *Current Opin. in Biotech.*, 2007 18:295-304; and Silacci et al., *J. Biol. Chem.*, 2014, 289: 14392-14398; each of which is incorporated by reference in its entirety. Alternative scaffolds comprise one type of RPP.

The term "antigen-binding domain" means the portion of an antibody that is capable of specifically binding to an antigen or epitope.

The terms "full length antibody," "intact antibody," and "whole antibody" are used herein interchangeably to refer to an antibody having a structure substantially similar to a naturally occurring antibody structure and having heavy chains that comprise an Fc region.

The term "Fc region" means the C-terminal region of an immunoglobulin heavy chain that, in naturally occurring antibodies, interacts with Fc receptors and certain proteins of the complement system. The structures of the Fc regions of various immunoglobulins, and the glycosylation sites contained therein, are known in the art. See Schroeder and Cavacini, *J. Allergy Clin. Immunol.*, 2010, 125:S41-52, incorporated by reference in its entirety. The Fc region may be a naturally occurring Fc region, or an Fc region modified as described elsewhere in this disclosure.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, MD, incorporated by reference in its entirety.

The light chain from any vertebrate species can be assigned to one of two types, called kappa (κ) and lambda (λ), based on the sequence of its constant domain.

The heavy chain from any vertebrate species can be assigned to one of five different classes (or isotypes): IgA, IgD, IgE, IgG, and IgM. These classes are also designated a, 6, F, y, and p, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme); each of which is incorporated by reference in its entirety.

Table 1 provides the positions of CDR1-L (CDR1 of $V_L$), CDR2-L (CDR2 of $V_L$), CDR3-L (CDR3 of $V_L$), CDR1-H (CDR1 of $V_H$), CDR2-H (CDR2 of $V_H$), and CDR3-H (CDR3 of $V_H$), as identified by the Kabat and Chothia schemes. For CDR1-H, residue numbering is provided using both the Kabat and Chothia numbering schemes.

CDRs may be assigned, for example, using antibody numbering software, such as Abnum, available at www.bio-inf.org.uk/abs/abnum/, and described in Abhinandan and Martin, *Immunology*, 2008, 45:3832-3839, incorporated by reference in its entirety.

TABLE 1

| Residues in CDRs according to Kabat and Chothia numbering schemes. | | |
|---|---|---|
| CDR | Kabat | Chothia |
| CDR1-L | 24-34 | 24-34 |
| CDR2-L | 50-56 | 50-56 |
| CDR3-L | 89-97 | 89-97 |
| CDR1-H (Kabat Numbering) | 31-35B | 26-32 or 34* |
| CDR1-H (Chothia Numbering) | 31-35 | 26-32 |
| CDR2-H | 50-65 | 52-56 |
| CDR3-H | 95-102 | 95-102 |

*The C-terminus of CDR1-H, when numbered using the Kabat numbering convention, varies between 32 and 34, depending on the length of the CDR.

The "EU numbering scheme" is generally used when referring to a residue in an antibody heavy chain constant region (e.g., as reported in Kabat et al., supra).

An "antibody fragment" comprises a portion of an intact antibody, such as the antigen-binding or variable region of an intact antibody. Antibody fragments include, for example, Fv fragments, Fab fragments, F(ab')2 fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with ß-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). In some embodiments, the linker is a (GGGGS)$_n$(SEQ ID NO: 5). In some embodiments, n=1, 2, 3, 4, 5, or 6. See Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain comprises an IgG4 Fc domain.

The term "single domain antibody" refers to a molecule in which one variable domain of an antibody specifically binds to an antigen without the presence of the other variable domain. Single domain antibodies, and fragments thereof, are described in Arabi Ghahroudi et al., *FEBS Letters*, 1998, 414:521-526 and Muyldermans et al., *Trends in Biochem. Sci.*, 2001, 26:230-245, each of which is incorporated by reference in its entirety.

A "monospecific RPP" is an RPP that comprises a binding site that specifically binds to a single epitope. An example of a monospecific RPP is a naturally occurring IgG molecule which, while divalent, recognizes the same epitope at each antigen-binding domain. The binding specificity may be present in any suitable valency.

A "polyspecific RPP" is an RPP that comprises a binding site that binds non-specifically to more than one epitope. An example of a polyspecific RPP is a mixture of antibodies that bind to different serotypes of pneumococcal bacteria.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "polyclonal antibody" refers to a mixture of at least two monoclonal antibodies. Polyclonal antibodies may be either monospecific or polyspecific.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature*, 1988, 332:323-329; and Presta, *Curr. Op. Struct. Biol.*, 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated RPP" or "isolated nucleic acid" is an RPP or nucleic acid that has been separated and/or recovered from a component of its natural environment. Components of the natural environment may include enzymes, hormones, and other proteinaceous or nonproteinaceous materials. In some embodiments, an isolated RPP is purified to a degree sufficient to obtain at least 15 residues of N-terminal or internal amino acid sequence, for example by use of a spinning cup sequenator. In some embodiments, an isolated RPP is purified to homogeneity by gel electrophoresis (e.g., SDS-PAGE) under reducing or nonreducing conditions, with detection by Coomassie blue or silver stain. An isolated RPP includes an RPP in situ within recombinant cells, since at least one component of the RPP's natural environment is not present. In some aspects, an isolated RPP or isolated nucleic acid is prepared by at least one purification step. In some embodiments, an isolated RPP or isolated nucleic acid is purified to at least 80%, 85%, 90%, 95%, or 99% by weight. In some embodiments, an isolated RPP or isolated nucleic acid is purified to at least 80%, 85%, 90%, 95%, or 99% by volume. In some embodiments, an isolated RPP or isolated nucleic acid is provided as a solution comprising at least 85%, 90%, 95%, 98%, 99% to 100% RPP or nucleic acid by weight. In some embodiments, an isolated RPP or isolated nucleic acid is provided as a solution comprising at least 85%, 90%, 95%, 98%, 99% to 100% RPP or nucleic acid by volume.

"Affinity" refers to the strength of the sum total of non-covalent interactions between a single binding site of a molecule (e.g., an RPP) and its binding partner (e.g., an antigen or epitope). Unless indicated otherwise, as used herein, "affinity" refers to intrinsic binding affinity, which reflects a 1:1 interaction between members of a binding pair (e.g., RPP and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®).

With regard to the binding of an RPP to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the RPP to the target molecule is competitively inhibited by the control molecule.

The term "$k_d$" ($sec^{-1}$), as used herein, refers to the dissociation rate constant of a particular ABP-antigen interaction. This value is also referred to as the $k_{off}$ value.

The term "$k_a$" ($M^{-1} \times sec^{-1}$), as used herein, refers to the association rate constant of a particular ABP-antigen interaction. This value is also referred to as the $k_{on}$ value.

The term "$K_D$" (M), as used herein, refers to the dissociation equilibrium constant of a particular ABP-antigen interaction. $K_D = k_d / k_a$.

The term "$K_A$" ($M^{-1}$), as used herein, refers to the association equilibrium constant of a particular ABP-antigen interaction. $K_A = k_a / k_d$.

An "immunoconjugate" is an RPP conjugated to one or more heterologous molecule(s).

"Effector functions" refer to those biological activities mediated by the Fc region of an antibody, which activities may vary depending on the antibody isotype. Examples of antibody effector functions include C1q binding to activate complement dependent cytotoxicity (CDC), Fc receptor binding to activate antibody-dependent cellular cytotoxicity (ADCC), and antibody dependent cellular phagocytosis (ADCP).

When used herein in the context of two or more RPPs, the term "competes with" or "cross-competes with" indicates that the two or more RPPs compete for binding to an antigen (e.g., pneumococcus polysaccharide). In one exemplary assay, pneumococcus polysaccharide is coated on a surface and contacted with a first pneumococcus polysaccharide RPP, after which a second pneumococcus polysaccharide RPP is added. In another exemplary assay, a first pneumococcus polysaccharide RPP is coated on a surface and contacted with pneumococcus polysaccharide, and then a second pneumococcus polysaccharide RPP is added. If the presence of the first pneumococcus polysaccharide RPP reduces binding of the second pneumococcus polysaccharide RPP, in either assay, then the RPPs compete. The term "competes with" also includes combinations of RPPs where one RPP reduces binding of another RPP, but where no competition is observed when the RPPs are added in the reverse order. However, in some embodiments, the first and second RPPs inhibit binding of each other, regardless of the order in which they are added. In some embodiments, one RPP reduces binding of another RPP to its antigen by at least 25%, at least 50%, at least 60%, at least 70%, at least 80%, at least 85%, at least 90%, or at least 95%. A skilled artisan can select the concentrations of the antibodies used in the competition assays based on the affinities of the RPPs for pneumococcus polysaccharide and the valency of the RPPs. The assays described in this definition are illustrative, and a skilled artisan can utilize any suitable assay to determine if antibodies compete with each other. Suitable assays are described, for example, in Cox et al., "Immunoassay Methods," in *Assay Guidance Manual*[*Internet*], Updated Dec. 24, 2014 (www.ncbi.nlm.nih.gov/books/NBK92434/; accessed Sep. 29, 2015); Silman et al., *Cytometry*, 2001, 44:30-37; and Finco et al., *J. Pharm. Biomed. Anal.*, 2011, 54:351-358; each of which is incorporated by reference in its entirety.

The term "epitope" means a portion of an antigen the specifically binds to an RPP. Epitopes frequently consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an RPP binds can be determined using known techniques for epitope determination such as, for example, testing for RPP binding to pneumococcus polysaccharide serotypes.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGA-LIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution an amino acid with a chemically or functionally similar amino acid. Conservative substitution tables providing similar amino acids are well known in the art. By way of example, the groups of amino acids provided in TABLES 2-4 are, in some embodiments, considered conservative substitutions for one another.

TABLE 2

Selected groups of amino acids that are considered conservative substitutions for one another, in certain embodiments.

| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 3

Additional selected groups of amino acids that are considered conservative substitutions for one another, in certain embodiments.

| Group 1 | A, S, and T |
| Group 2 | D and E |
| Group 3 | N and Q |
| Group 4 | R and K |
| Group 5 | I, L, and M |
| Group 6 | F, Y, and W |

TABLE 4

Further selected groups of amino acids that are considered conservative substitutions for one another, in certain embodiments.

| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, NY. An RPP generated by making one or more conservative substitutions of amino acid residues in a parent RPP is referred to as a "conservatively modified variant."

The term "treating" (and variations thereof such as "treat" or "treatment") refers to clinical intervention in an attempt to alter the natural course of a disease or condition in a subject in need thereof. Treatment can be performed both for prophylaxis and during the course of clinical pathology. Desirable effects of treatment include preventing occurrence or recurrence of disease, alleviation of symptoms, diminish of any direct or indirect pathological consequences of the disease, preventing metastasis, decreasing the rate of disease progression, amelioration or palliation of the disease state, and remission or improved prognosis.

As used herein, the term "therapeutically effective amount" or "effective amount" refers to an amount of an RPP or pharmaceutical composition provided herein that, when administered to a subject, is effective to treat a disease or disorder.

As used herein, the term "subject" means a mammalian subject. Exemplary subjects include humans, monkeys, dogs, cats, mice, rats, cows, horses, camels, goats, rabbits, and sheep. In certain embodiments, the subject is a human. In some embodiments the subject has a disease or condition that can be treated with an RPP provided herein. In some aspects, the disease or condition is a cancer. In some aspects, the disease or condition is a viral infection.

The term "package insert" is used to refer to instructions customarily included in commercial packages of therapeutic or diagnostic products (e.g., kits) that contain information about the indications, usage, dosage, administration, combination therapy, contraindications and/or warnings concerning the use of such therapeutic or diagnostic products.

The term "cytotoxic agent," as used herein, refers to a substance that inhibits or prevents a cellular function and/or causes cell death or destruction.

A "chemotherapeutic agent" refers to a chemical compound useful in the treatment of cancer. Chemotherapeutic agents include "anti-hormonal agents" or "endocrine therapeutics" which act to regulate, reduce, block, or inhibit the effects of hormones that can promote the growth of cancer.

The term "cytostatic agent" refers to a compound or composition which arrests growth of a cell either in vitro or in vivo. In some embodiments, a cytostatic agent is an agent that reduces the percentage of cells in S phase. In some embodiments, a cytostatic agent reduces the percentage of cells in S phase by at least about 20%, at least about 40%, at least about 60%, or at least about 80%.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein. The terms "cell proliferative disorder" and "proliferative disorder" refer to disorders that are associated with some degree of abnormal cell proliferation. In some embodiments, the cell proliferative disorder is a cancer.

The term "pharmaceutical composition" refers to a preparation which is in such form as to permit the biological activity of an active ingredient contained therein to be effective in treating a subject, and which contains no additional components which are unacceptably toxic to the subject.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The term "agonize" refers to the activation of receptor signaling to induce a biological response associated with activation of the receptor. An "agonist" is an entity that binds to and agonizes a receptor.

The term "antagonize" refers to the inhibition of receptor signaling to inhibit a biological response associated with activation of the receptor. An "antagonist" is an entity that binds to and antagonizes a receptor.

The term "effector T cell" includes T helper (i.e., CD4+) cells and cytotoxic (i.e., CD8+) T cells. CD4+ effector T cells contribute to the development of several immunologic processes, including maturation of B cells into plasma cells and memory B cells, and activation of cytotoxic T cells and macrophages. CD8+ effector T cells destroy virus-infected cells and tumor cells. See Seder and Ahmed, *Nature Immunol.*, 2003, 4:835-842, incorporated by reference in its entirety, for additional information on effector T cells.

The term "regulatory T cell" includes cells that regulate immunological tolerance, for example, by suppressing effector T cells. In some aspects, the regulatory T cell has a CD4+CD25+Foxp3+ phenotype. In some aspects, the regulatory T cell has a CD8+CD25+ phenotype. See Nocentini et al., *Br. J. Pharmacol.*, 2012, 165:2089-2099, incorporated by reference in its entirety, for additional information on regulatory T cells.

The term "dendritic cell" refers to a professional antigen-presenting cell capable of activating a naïve T cell and stimulating growth and differentiation of a B cell.

The term "plasma cell" refers to white blood cells that secrete large volumes of antibodies. They are transported by the blood plasma and the lymphatic system. B cells (for example, either germinal center naïve B cells or memory B cells) differentiate into plasma cells that produce antibody molecules closely modelled after the receptors of the precursor B cell. Once released into the blood and lymph, these antibody molecules bind to the target antigen (foreign substance) and initiate its neutralization or destruction. Terminally differentiated plasma cells express relatively few surface antigens, and do not express common pan-B cell markers, such as CD19 and CD20. Instead, plasma cells are identified through flow cytometry by their additional expression of CD138, CD78, and the Interleukin-6 receptor. In humans, CD27 is a good marker for plasma cells, naive B cells are CD27−, memory B-cells are CD27+ and plasma cells are CD27++. The surface antigen CD138 (syndecan-1) is expressed at high levels. Another important surface antigen is CD319 (SLAMF7). This antigen is expressed at high levels on normal human plasma cells. It is also expressed on malignant plasma cells in multiple myeloma. Compared with CD138, which disappears rapidly ex vivo, the expression of CD319 is considerably more stable.

The term "plasmablast" refers to antibody-secreting cells in the peripheral blood, which differentiate from activated B cells, such as memory B cells, upon stimulation with an antigen. The most immature blood cell that is considered of plasma cell lineage is the plasmablast. Plasmablasts secrete more antibodies than B cells, but less than plasma cells. They divide rapidly and are still capable of internalizing antigens and presenting them to T cells. A cell may stay in this state for several days, and then either die or irrevocably differentiate into a mature, fully differentiated plasma cell.

Differentiation of mature B cells into plasma cells is dependent upon the transcription factors Blimp-1/PRDM1 and IRF4.

The term "memory B cell" refers to a B cell sub-type that are formed within germinal centers following primary infection and are important in generating an accelerated and more robust antibody-mediated immune response in the case of re-infection (also known as a secondary immune response). Memory B cells do not secrete antibody until activated by their specific antigen.

The term "naïve B cell" refers to a B cell that has not been exposed to an antigen. Once exposed to an antigen, the naïve B cell either becomes a memory B cell or a plasma cell that secretes antibodies specific to the antigen that was originally bound. Plasma cells do not last long in the circulation, this is in contrast to memory cells that last for very long periods of time.

The term "titer" refers a measurement of how much antibody an organism is producing that recognizes a particular epitope or antigen, expressed as the inverse of the greatest dilution (in a serial dilution) that still gives a positive result. Enzyme linked immunosorbent assay (ELISA) is a common means of determining antibody titers.

The term "peripheral blood" refers to blood which travels through peripheral vessels. Peripheral blood is typically obtained by venipuncture (also called phlebotomy), or by finger prick for small quantities.

The term "vaccine" refers to an agent that stimulates the body's immune system to recognize the agent as a threat, destroy it, and to further recognize and destroy any of the microorganisms associated with that agent that it may encounter in the future. The term vaccine can refer to a biological preparation that provides active acquired immunity to a particular disease. A vaccine often contains an agent that resembles a disease-causing microorganism and is often made from weakened or killed forms of the microbe, its toxins, or one of its surface proteins. Vaccines can be prophylactic (example: to prevent or ameliorate the effects of a future infection by a natural or "wild" pathogen), or therapeutic (e.g., vaccines against cancer are being investigated). More generally, the term vaccine can refer to any agent that induces an immune response. For example, cancer cells can be used to vaccinate an individual against certain cancer antigens. Some vaccines contain inactivated, but previously virulent, micro-organisms that have been destroyed with chemicals, heat, or radiation. Examples include the polio vaccine, hepatitis A vaccine, rabies vaccine and some influenza vaccines. Some vaccines contain live, attenuated microorganisms. Many of these are active viruses that have been cultivated under conditions that disable their virulent properties, or that use closely related but less dangerous organisms to produce a broad immune response. Although most attenuated vaccines are viral, some are bacterial in nature. Examples include the viral diseases yellow fever, measles, mumps, and rubella, and the bacterial disease typhoid. The live *Mycobacterium tuberculosis* vaccine developed by Calmette and Guerin is not made of a contagious strain but contains a virulently modified strain called "BCG" used to elicit an immune response to the vaccine. The live attenuated vaccine containing strain *Yersinia pestis* EV is used for plague immunization. Attenuated vaccines have some advantages and disadvantages. They typically provoke more durable immunological responses and are the preferred type for healthy adults. But they may not be safe for use in immunocompromised individuals, and on rare occasions mutate to a virulent form and cause disease. Toxoid vaccines are made from inactivated toxic compounds that cause illness rather than the micro-organism. Examples of toxoid-based vaccines include tetanus and diphtheria. Toxoid vaccines are known for their efficacy. Not all toxoids are for micro-organisms; for example, *Crotalus atrox* toxoid is used to vaccinate dogs against rattlesnake bites. In protein subunit vaccines, rather than introducing an inactivated or attenuated micro-organism to an immune system (which would constitute a "whole-agent" vaccine), a fragment of it can create an immune response. Examples include the subunit vaccine against Hepatitis B virus that is composed of only the surface proteins of the virus (previously extracted from the blood serum of chronically infected patients, but now produced by recombination of the viral genes into yeast) or as an edible algae vaccine, the virus-like particle (VLP) vaccine against human papillomavirus (HPV) that is composed of the viral major capsid protein, and the hemagglutinin and neuraminidase subunits of the influenza virus. For conjugate vaccines, certain bacteria have polysaccharide outer coats that are poorly immunogenic. By linking these outer coats to proteins (e.g., toxins), the immune system can be led to recognize the polysaccharide as if it were a protein antigen. This approach is used in the *Haemophilus influenzae* type B vaccine. Dendritic cell vaccines combine dendritic cells with antigens in order to present the antigens to the body's white blood cells, thus stimulating an immune reaction. These vaccines have shown some positive preliminary results for treating brain tumors and are also tested in malignant melanoma. For recombinant vector vaccines, by combining the physiology of one micro-organism and the DNA of another, immunity can be created against diseases that have complex infection processes. An example is the RVSV-ZEBOV vaccine licensed to Merck that is being used in 2018 to combat ebola in Congo. An alternative, experimental approach to vaccination called DNA vaccination, created from an infectious agent's DNA, is under development. The proposed mechanism is the insertion (and expression, enhanced by the use of electroporation, triggering immune system recognition) of viral or bacterial DNA into human or animal cells. Some cells of the immune system that recognize the proteins expressed will mount an attack against these proteins and cells expressing them. Because these cells live for a very long time, if the pathogen that normally expresses these proteins is encountered at a later time, they will be attacked instantly by the immune system. One potential advantage of DNA vaccines is that they are very easy to produce and store. Vaccines may be monovalent (also called univalent) or multivalent (also called polyvalent). A monovalent vaccine is designed to immunize against a single antigen or single microorganism. A multivalent or polyvalent vaccine is designed to immunize against two or more strains of the same microorganism, or against two or more microorganisms. The valency of a multivalent vaccine may be denoted with a Greek or Latin prefix (e.g., tetravalent or quadrivalent). In certain cases, a monovalent vaccine may be preferable for rapidly developing a strong immune response.

The term "hyperimmune" refers to a polyclonal antibody preparation similar to intravenous immunoglobulin (IVIg), except that it is prepared from the plasma of donors with high titers of antibody against a specific organism or antigen. The term hyperimmune is often used interchangeably with the terms "hyperimmune gammaglobulin" and "hyperimmune globulin". Some agents against which hyperimmune globulins are available include hepatitis B, rabies, tetanus toxin, varicella-zoster, etc. Administration of hyperimmune globulin provides "passive" immunity to the patient against an agent. This is in contrast to vaccines that provide "active" immunity. However, vaccines take much longer to achieve that purpose while hyperimmune globulin provides instant "passive" short-lived immunity.

The term "in vivo" translates to "in the living", and refers to scientific studies in which the effects of various biological entities are tested on whole, living organisms or cells, usually animals, including humans, and plants, as opposed to a tissue extract or dead organism. This is not to be confused with experiments done in vitro ("within the glass"), i.e., in a laboratory environment using test tubes, Petri dishes, etc. Examples of investigations in vivo include: the pathogenesis of disease by comparing the effects of bacterial infection with the effects of purified bacterial toxins; the development of non-antibiotics, antiviral drugs, and new drugs generally; and new surgical procedures. Consequently, animal testing and clinical trials are major elements of in vivo research. In vivo testing is often employed over in vitro because it is better suited for observing the overall effects of an experiment on a living subject.

The term "activity" refers to a quantitative measurement of an RPP or antibody against an antigen, vaccine, protein, epitope, cell, bacterium, or virus. Activity can be assessed using in vivo or in vitro methods.

The term "recombinant" refers to proteins that result from the expression of recombinant DNA within living cells. Recombinant DNA is the general name for a piece of DNA that has been created by the combination of at least two separate segments of DNA.

The term "in vitro" translates to "in the glass", and refers to scientific studies that are performed with microorganisms, cells, or biological molecules outside their normal biological context. Colloquially called "test-tube experiments", these studies in biology and its subdisciplines are traditionally done in labware such as test tubes, flasks, Petri dishes, and microtiter plates. Studies conducted using components of an organism that have been isolated from their usual biological surroundings permit a more detailed or more convenient analysis than can be done with whole organisms; however, results obtained from in vitro experiments may not fully or accurately predict the effects on a whole organism. In contrast to in vitro experiments, in vivo studies are those conducted in animals, including humans, and whole plants.

The term "neutralization" refers to the ability of specific antibodies to block the site(s) on viruses that they use to enter their target cell. The effect of a neutralizing antibody can be negligible even with large excesses of antibody production if they lack specificity to this antigen. The production of specific antibodies can be learned for a faster response at next exposition. The reduction or destruction of a homologous infectious agent can be partial or complete and can make it no longer infectious or pathogenic to other cells.

A "variant" of a polypeptide (e.g., an antibody) comprises an amino acid sequence wherein one or more amino acid residues are inserted into, deleted from and/or substituted into the amino acid sequence relative to the native polypeptide sequence, and retains essentially the same biological activity as the native polypeptide. The biological activity of the polypeptide can be measured using standard techniques in the art (for example, if the variant is an antibody, its activity may be tested by binding assays, as described herein). Variants of the invention include fragments, analogs, recombinant polypeptides, synthetic polypeptides, and/or fusion proteins.

A "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, CA and Baron et al., 1995, Nucleic Acids Res. 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include CS-9 cells, the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell.

The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

7.2. Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereocenters intends each stereoisomer, and all combinations of stereoisomers, thereof.

7.3. RPPs and Libraries of RPPs

Each member of the libraries of RPPs described herein is a polypeptide that specifically binds an antigen, e.g., is an antibody or an antibody fragment. In some embodiments, the RPPs include cognate pairs of the heavy and light chain CDR3 sequences disclosed herein. In some embodiments the RPPs are scFvs. In some embodiments the RPPs are full-length antibodies.

In some embodiments, the RPPs are antibody fragments. A Fab fragment is a monovalent fragment having the $V_L$, $V_H$, $C_L$ and $C_H1$ domains; a F(ab')2 fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, US App. Pub. No. 05/0202512, 04/0202995, 04/0038291, 04/0009507, 03/0039958, Ward et al., Nature 341:544-546, 1989).

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5th Ed., US Dept. of Health and Human Services, PHS, NIH, NIH Publication no. 91-3242, 1991.

The term "human antibody," also referred to as "fully human antibody," includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., 1991, Science 253:164.

An RPP may also be any synthetic or genetically engineered protein. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker (scFv proteins).

Another form of an antibody fragment is a peptide comprising one or more complementarity determining regions (CDRs) of an antibody. CDRs (also termed "minimal recognition units", or "hypervariable region") can be incorporated into a molecule either covalently or noncovalently to make it an antigen binding protein. CDRs can be obtained by constructing polynucleotides that encode the CDR of interest. Such polynucleotides are prepared, for example, by using the polymerase chain reaction to synthesize the variable region using mRNA of antibody producing cells as a template (see, for example, Larrick et al., Methods: A Companion to Methods in Enzymology 2:106, 1991; Courtenay Luck, "Genetic Manipulation of Monoclonal Antibodies," in Monoclonal Antibodies: Production, Engineering and Clinical Application, Ritter et al. (eds.), page 166 (Cambridge University Press 1995); and Ward et al., "Genetic Manipulation and Expression of Antibodies," in Monoclonal Antibodies: Principles and Applications, Birch et al., (eds.), page 137 (Wiley Liss, Inc. 1995).

The variable region domains of RPPs can be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C terminal amino acid to at least one other antibody domain or a fragment thereof. Thus, for example, a $V_H$ domain that is present in the variable region domain may be linked to an immunoglobulin CH1 domain, or a fragment thereof. Similarly, a $V_L$ domain may be linked to a CK domain or a fragment thereof. In this way, for example, the antibody may be a Fab fragment wherein the antigen binding domain contains associated $V_H$ and $V_L$ domains covalently linked at their C termini to a CH1 and CK domain, respectively. The CH1 domain may be extended with further amino acids, for example to provide a hinge region or a portion of a hinge region domain as found in a Fab' fragment, or to provide further domains, such as antibody $C_H2$ and $C_H3$ domains.

As described herein, RPPs comprise the cognate pairs of heavy and light chain CDR3 sequence disclosed herein. For example, CDRs may be incorporated into known antibody framework regions (IgG1, IgG2, etc.), or conjugated to a suitable vehicle to enhance the half-life thereof. Suitable vehicles include, but are not limited to Fc, polyethylene glycol (PEG), albumin, transferrin, and the like. These and other suitable vehicles are known in the art. Such conjugated CDR peptides may be in monomeric, dimeric, tetrameric, or other form. In one embodiment, one or more water-soluble polymer is bonded at one or more specific position, for example at the amino terminus, of a binding agent.

In certain embodiments, an antibody in an RPP comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative binding agent comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

An RPP can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Different RPPs may bind to different domains of disease targets or act by different mechanisms of action. As indicated herein inter alia, the domain regions are designated such as to be inclusive of the group, unless otherwise indicated. For example, amino acids 4-12 refers to nine amino acids: amino acids at positions 4, and 12, as well as the seven intervening amino acids in the sequence. Other examples include antigen binding proteins that inhibit binding of a pathogen to its target cell, i.e., neutralizing activity. An antigen binding protein need not completely inhibit a binding to target cell to find use in the present invention.

The RPPs describe herein can include an FC region, e.g., a dimer Fc polypeptide. One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

Antigen-binding fragments of RPPs of the invention can be produced by conventional techniques. Examples of such fragments include, but are not limited to, Fab and F(ab')$_2$ fragments. Antibody fragments and derivatives produced by genetic engineering techniques also are contemplated.

Additional embodiments include chimeric antibodies, e.g., humanized versions of non-human (e.g., murine) monoclonal antibodies. Such humanized antibodies may be prepared by known techniques, and offer the advantage of reduced immunogenicity when the antibodies are administered to humans. In one embodiment, a humanized antibody comprises the variable domain of a murine antibody (or all or part of the antigen binding site thereof) and a constant domain derived from a human antibody. Alternatively, a humanized antibody fragment may comprise the antigen binding site of a murine antibody and a variable domain fragment (lacking the antigen-binding site) derived from a human antibody. Procedures for the production of chimeric and further engineered antibodies include those described in Riechmann et al., 1988, Nature 332:323, Liu et al., 1987, Proc. Nat. Acad. Sci. USA 84:3439, Larrick et al., 1989, Bio/Technology 7:934, and Winter et al., 1993, TIPS 14:139. In one embodiment, the chimeric antibody is a CDR grafted antibody. Techniques for humanizing antibodies are discussed in, e.g., U.S. Pat. Nos. 5,869,619, 5,225,539, 5,821,337, 5,859,205, 6,881,557, Padlan et al., 1995, FASEB J. 9:133-39, and Tamura et al., 2000, J. Immunol. 164:1432-41.

Procedures have been developed for generating human or partially human antibodies in non-human animals. For example, mice in which one or more endogenous immunoglobulin genes have been inactivated by various means have been prepared. Human immunoglobulin genes have been introduced into the mice to replace the inactivated mouse genes. Antibodies produced in the animal incorporate human immunoglobulin polypeptide chains encoded by the human genetic material introduced into the animal. In one embodiment, a non-human animal, such as a transgenic mouse, is immunized with a vaccine, such that antibodies directed against the vaccine antigen pare generated in the animal.

Examples of techniques for production and use of transgenic animals for the production of human or partially human antibodies are described in U.S. Pat. Nos. 5,814,318, 5,569,825, and 5,545,806, Davis et al., 2003, Production of human antibodies from transgenic mice in Lo, ed. Antibody Engineering: Methods and Protocols, Humana Press, NJ:191-200, Kellermann et al., 2002, Curr Opin Biotechnol. 13:593-97, Russel et al., 2000, Infect Immun. 68:1820-26, Gallo et al., 2000, Eur J Immun. 30:534-40, Davis et al., 1999, Cancer Metastasis Rev. 18:421-25, Green, 1999, J Immunol Methods. 231:11-23, Jakobovits, 1998, Advanced Drug Delivery Reviews 31:33-42, Green et al., 1998, J Exp Med. 188:483-95, Jakobovits A, 1998, Exp. Opin. Invest. Drugs. 7:607-14, Tsuda et al., 1997, Genomics. 42:413-21, Mendez et al., 1997, Nat Genet. 15:146-56, Jakobovits, 1994, Curr Biol. 4:761-63, Arbones et al., 1994, Immunity. 1:247-60, Green et al., 1994, Nat Genet. 7:13-21, Jakobovits et al., 1993, Nature. 362:255-58, Jakobovits et al., 1993, Proc Natl Acad Sci USA. 90:2551-55. Chen, J., M. Trounstine, F. W. Alt, F. Young, C. Kurahara, J. Loring, D. Huszar. Inter'l Immunol. 5 (1993): 647-656, Choi et al., 1993, Nature Genetics 4: 117-23, Fishwild et al., 1996, Nature Biotech. 14: 845-51, Harding et al., 1995, Annals of the New York Academy of Sciences, Lonberg et al., 1994, Nature 368: 856-59, Lonberg, 1994, Transgenic Approaches to Human Monoclonal Antibodies in Handbook of Experimental Pharmacology 113: 49-101, Lonberg et al., 1995, Internal Review of Immunology 13: 65-93, Neuberger, 1996, Nature Biotechnology 14: 826, Taylor et al., 1992, Nucleic Acids Res. 20: 6287-95, Taylor et al., 1994, Inter'l Immunol. 6: 579-91, Tomizuka et al., 1997, Nature Genetics 16: 133-43, Tomizuka et al., 2000, Pro. Nat'l Acad. Sci. USA 97: 722-27, Tuaillon et al., 1993, Pro. Nat'l Acad. Sci. USA 90: 3720-24, and Tuaillon et al., 1994, J. Immunol. 152: 2912-20.

RPPs (e.g., antibodies, antibody fragments, and antibody derivatives) of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lantto et al., 2002, Methods Mol. Biol. 178:303-16.

Single chain antibodies (scFv) may be formed by linking heavy and light chain variable domain (Fv region) fragments via an amino acid bridge (short peptide linker, e.g., a synthetic sequence of amino acid residues), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the

| two variable domains (Kortt et al., 1997, *Prot. Eng.* 10:423; Kortt et al., 2001, *Biomol. Eng.* 18:95-108, Bird et al., 1988, *Science* 242:423-26 and Huston et al., 1988, *Proc. Natl. Acad. Sci. USA* 85:5879-83). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci.* USA 85:5879; Ward et al., 1989, *Nature* 334:544, de Graaf et al., 2002, *Methods Mol Biol.* 178:379-87.

In certain aspects, the invention includes RPPs generated from libraries of antibody-encoding expression vectors. RPPs comprise 10, 100, 1,000, 10,000 or more than 100,000 distinct antibody sequences. In certain aspects, the RPPs are generated from mammalian cells engineered recombinantly with antibody sequences encoded by single plasma cells or plasmablasts. In certain aspects, the RPPs are polyvalent, in that they comprise antibodies that have different antigen-binding properties. In some embodiments, the RPPs bind to multiple epitopes on a target antigen. In some embodiments, the RPPs bind to multiple antigens.

7.4. CDR3 Sequences of RPPs

CDR3H (heavy chain immunoglobulin) and CDR3L (light chain immunoglobulin) polypeptide sequences comprising each member of twelve RPPs generated using the methods described herein are provided in the sequence listing. A summary of the sequences is provided in TABLE 5. The sequences are found in the sequence listing submitted with this application. RPPs provided herein using human thymocytes or human T cells as immunogens are generated from humanized mice that express fully human V(D)J antibody sequences. RPPs provided herein using pneumococcus polysaccharide, influenza A virus antigen, hepatitis B virus antigen, or *Haemophilus influenzae* B polysaccharide were generated from vaccinated human donors. The RPPs comprise between 1,141 and 10,537 unique antibodies.

75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to least one of the CDRs provided herein.

7.5. Nucleic Acids

In one aspect, the present invention provides isolated nucleic acid molecules. The nucleic acids comprise, for example, polynucleotides that encode all or part of an RPP, for example, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, CDRs only, or full length) can be isolated from B-cells of mice that have been immunized with a vaccine. The nucleic acid can be isolated by conventional procedures such as polymerase chain reaction (PCR).

Polypeptide sequences of the CDR3 from the variable regions of the heavy and light chain variable regions are shown herein. The skilled artisan will appreciate that, due to the degeneracy of the genetic code, each of the polypeptide sequences disclosed herein is encoded by a large number of other nucleic acid sequences. The present invention provides each degenerate nucleotide sequence encoding each RPP of the invention.

TABLE 5

| CDR3 heavy and CDR3 light chain sequences | | | |
|---|---|---|---|
| RPP ID | Immunogen | SEQ ID NOS: | Number of antibodies |
| RPP1 | Pneumococcus polysaccharide (Pneumovax23, Merck) | 1-21074 | 10537 |
| RPP2 | Influenza A antigen (Seqirus, CSL) | 21075-33980 | 6453 |
| RPP3 | Haemophilius influenzae b polysaccharide (PedvaxHIB, Merck) | 33981-47174 | 6597 |
| RPP4 | Haemophilius influenzae b polysaccharide (PedvaxHIB, Merck) | 47175-64340 | 8583 |
| RPP5 | Haemophilius influenzae b polysaccharide (PedvaxHIB, Merck) | 64341-80252 | 7956 |
| RPP6 | Haemophilius influenzae b polysaccharide (PedvaxHIB, Merck) | 80253-100626 | 10187 |
| RPP8 | Hepatitis B virus antigen (Engerix, GSK) | 100627-103860 | 1617 |
| RPP9 | Hepatitis B virus antigen (Engerix, GSK) | 103861-106380 | 1260 |
| RPP10 | Human thymocytes (thymocyte globulin) | 106381-110130 | 1875 |
| RPP11 | Human thymocytes (thymocyte globulin) | 110131-114096 | 1983 |
| RPP12 | Human T cells (thymocyte globulin) | 114097-117876 | 1890 |
| RPP13 | Human T cells (thymocyte globulin) | 117877-120158 | 1141 |

An oligopeptide or polypeptide is within the scope of the invention if it has an amino acid sequence that is at least Methods for hybridizing nucleic acids are well-known in the art. See, e.g., Curr. Prot. in Mol. Biol., John Wiley &

Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 450 C, followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98, or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Curr. Prot. in Mol. Biol. 1995, Ausubel et al., eds., John Wiley & Sons, Inc., sections 2.10 and 6.3-6.4), and can be readily determined by those having ordinary skill in the art based on, for example, the length and/or base composition of the DNA.

Changes can be introduced by mutation into a nucleic acid, thereby leading to changes in the amino acid sequence of a polypeptide (e.g., an RPP) that it encodes. Mutations can be introduced using any technique known in the art. In one embodiment, one or more particular amino acid residues are changed using, for example, a site-directed mutagenesis protocol. In another embodiment, one or more randomly selected residues are changed using, for example, a random mutagenesis protocol. However, it is made, a mutant polypeptide can be expressed and screened for a desired property (e.g., binding to a virus).

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., a virus binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide In another aspect, the present invention provides libraries of nucleic acids that encode for libraries of antibody proteins, derived from plasmablasts and plasma cells. These libraries of nucleic acids are generated by isolating plasmablasts and plasma cells into single-cell reaction containers, wherein they are lysed and antibody-specific nucleic acids are purified or captured, for example on solid supports such as beads. The present invention provides methods for performing capture of transcripts from millions of single cells in parallel. Capture of transcripts is followed by amplification of nucleic acids that encode heavy and light chain immunoglobulins, and subsequent linkage of said nucleic acids into libraries of fused constructs that encode both heavy and light chain immunoglobulins. In such libraries the native pairing of heavy and light chain immunoglobulins, as originally found in the input plasmablasts and plasma cells, is maintained. Such methods are performed in parallel on millions of single cells, such that the resulting library of fused heavy and light chain immunoglobulin nucleic acids comprises natively paired sequences for millions of single cells. Such methods are described elsewhere (Adler et al., *Mabs* 9, 1282-1996, 2017).

7.6. Vectors and Expression Vectors

The present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

In another aspect of the present invention, expression vectors containing the nucleic acid molecules and polynucleotides of the present invention are also provided, and host cells transformed with such vectors, and methods of producing the polypeptides are also provided. The term "expression vector" refers to a plasmid, phage, virus or vector for expressing a polypeptide from a polynucleotide sequence. Vectors for the expression of the polypeptides contain at a minimum sequences required for vector propagation and for expression of the cloned insert. An expression vector comprises a transcriptional unit comprising an assembly of (1) a genetic element or elements having a regulatory role in gene expression, for example, promoters or enhancers, (2) a sequence that encodes polypeptides and proteins to be transcribed into mRNA and translated into protein, and (3) appropriate transcription initiation and termination sequences. These sequences may further include a selection marker. Vectors suitable for expression in host cells are readily available and the nucleic acid molecules are inserted into the vectors using standard recombinant DNA techniques. Such vectors can include promoters which function in specific tissues, and viral vectors for the expression of polypeptides in targeted human or animal cells.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The invention further provides methods of making polypeptides, e.g., RPPs. A variety of other expression/host systems may be utilized. Vector DNA can be introduced into prokaryotic or eukaryotic systems via conventional transformation or transfection techniques. These systems include but are not limited to microorganisms such as bacteria (for example, *E. coli*) transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells useful in recombinant protein production include but are not limited to VERO cells, HeLa cells, Chinese hamster ovary (CHO) cell lines, or their derivatives such as Veggie CHO and related cell lines which grow in serum-free media (see Rasmussen et al., 1998, Cytotechnology 28:31) or CHO strain DX-B 11, which is deficient in DHFR (see Urlaub et al., 1980, Proc. Natl. Acad. Sci. USA 77:4216-20) COS cells such as the COS-7 line of monkey kidney cells (ATCC CRL 1651) (see Gluzman et al., 1981, Cell 23:175), W138, BHK, HepG2, 3T3 (ATCC CCL 163), RIN, MDCK, A549, PC12, K562, L cells, C127 cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Mammalian expression allows for the production of secreted or soluble polypeptides which may be recovered from the growth medium.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Once such cells are transformed with vectors that contain selectable markers as well as the desired expression cassette, the cells can be allowed to grow in an enriched media before they are switched to selective media, for example. The selectable marker is designed to allow growth and recovery of cells that successfully express the introduced sequences. Resistant clumps of stably transformed cells can be proliferated using tissue culture techniques appropriate to the cell line employed. An overview of expression of recombinant proteins is found in Methods of Enzymology, v. 185, Goeddell, D. V., ed., Academic Press (1990). Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

The transformed cells can be cultured under conditions that promote expression of the polypeptide, and the polypeptide recovered by conventional protein purification procedures (as defined above).

In some cases, such as in expression using prokaryotic systems, the expressed polypeptides of this invention may need to be "refolded" and oxidized into a proper tertiary structure and disulfide linkages generated in order to be biologically active. Refolding can be accomplished using a number of procedures well known in the art. Such methods include, for example, exposing the solubilized polypeptide to a pH usually above 7 in the presence of a chaotropic agent. The selection of chaotrope is similar to the choices used for inclusion body solubilization; however, a chaotrope is typically used at a lower concentration. Exemplary chaotropic agents are guanidine and urea. In most cases, the refolding/oxidation solution will also contain a reducing agent plus its oxidized form in a specific ratio to generate a particular redox potential which allows for disulfide shuffling to occur for the formation of cysteine bridges. Some commonly used redox couples include cysteine/cystamine, glutathione/dithiobisGSH, cupric chloride, dithiothreitol DTT/dithiane DTT, and 2-mercaptoethanol (bME)/dithiobME. In many instances, a co-solvent may be used to increase the efficiency of the refolding. Commonly used cosolvents include glycerol, polyethylene glycol of various molecular weights, and arginine.

In addition, the polypeptides can be synthesized in solution or on a solid support in accordance with conventional techniques. Various automatic synthesizers are commercially available and can be used in accordance with known protocols. See, for example, Stewart and Young, Solid Phase Peptide Synthesis, 2d. Ed., Pierce Chemical Co. (1984); Tam et al., J Am Chem Soc, 105:6442, (1983); Merrifield, Science 232:341-347 (1986); Barany and Merrifield, The Peptides, Gross and Meienhofer, eds, Academic Press, New York, 1-284; Barany et al., Int J Pep Protein Res, 30:705-739 (1987).

The polypeptides and proteins of the present invention can be purified according to protein purification techniques well known to those of skill in the art. These techniques involve, at one level, the crude fractionation of the proteinaceous and non-proteinaceous fractions. Having separated the peptide polypeptides from other proteins, the peptide or polypeptide of interest can be further purified using chromatographic and electrophoretic techniques to achieve partial or complete purification (or purification to homogeneity). The term "purified polypeptide" as used herein, is intended to refer to a composition, isolatable from other components, wherein the polypeptide is purified to any degree relative to its naturally-obtainable state. A purified polypeptide therefore also refers to a polypeptide that is free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a peptide or polypeptide composition in which the polypeptide or peptide forms the major component of the composition, such as constituting about 50%, about 60%, about 70%, about 80%, about 85%, or about 90% or more of the proteins in the composition.

Various techniques suitable for use in purification will be well known to those of skill in the art. These include, for example, precipitation with ammonium sulphate, PEG, antibodies (immunoprecipitation) and the like or by heat denaturation, followed by centrifugation; chromatography such as affinity chromatography (Protein-A columns), ion exchange, gel filtration, reverse phase, hydroxylapatite, hydrophobic interaction chromatography, isoelectric focusing, gel electrophoresis, and combinations of these techniques. As is generally known in the art, it is believed that the order of conducting the various purification steps may be changed, or that certain steps may be omitted, and still result in a suitable method for the preparation of a substantially purified polypeptide. Exemplary purification steps are provided in the Examples below.

Various methods for quantifying the degree of purification of polypeptide will be known to those of skill in the art in light of the present disclosure. These include, for example, determining the specific binding activity of an active fraction, or assessing the amount of peptide or polypeptide within a fraction by SDS/PAGE analysis. A preferred method for assessing the purity of a polypeptide fraction is to calculate the binding activity of the fraction, to compare it to the binding activity of the initial extract, and to thus calculate the degree of purification, herein assessed by a "-fold purification number." The actual units used to represent the amount of binding activity will, of course, be dependent upon the particular assay technique chosen to follow the purification and whether or not the polypeptide or peptide exhibits a detectable binding activity.

In some aspects, the present invention includes libraries of antibody-encoding nucleic acid vectors for site-directed integration into mammalian genomes. Such vectors include plasmids, retroviruses, and lentivirus. These libraries of vectors encode libraries of antibody sequences, which are then be used to engineer mammalian cells for production of RPPs. The libraries of nucleic acid vectors may include 10, 100, 1,000, 10,000, or more than 100,000 different antibody-encoding sequences. The sequences are derived from plasmablasts and plasma cells. These libraries of nucleic acids are generated by isolating plasmablasts and plasma cells into single-cell reaction containers, wherein they are lysed and antibody-specific nucleic acids are purified or captured, for example on solid supports such as beads. The present invention provides methods for performing capture of transcripts from millions of single cells in parallel. Capture of transcripts is followed by amplification of nucleic acids that encode heavy and light chain immunoglobulins, and subsequent linkage of said nucleic acids into libraries of fused constructs that encode both heavy and light chain immunoglobulins. In such libraries the native pairing of heavy and light chain immunoglobulins, as originally found in the input plasmablasts and plasma cells, is maintained. Such methods are performed in parallel on millions of single cells, such that the resulting library of fused heavy and light chain immunoglobulin nucleic acids comprises natively paired sequences for millions of single cells. These paired fused amplicons are then engineered into full-length antibody constructs using Gibson Assembly, restriction endonucleases, or other recombinant DNA techniques.

Engineering into full-length antibody constructs is performed on the full library en masse, such that the antibody sequence content and antibody sequence counts of the library are essentially maintained throughout the process. In some aspects, the library of expression vectors is engineered in two steps, such that the scFv amplicon is subcloned into an intermediate vector, and then a second round of Gibson Assembly, restriction digestion, or other recombinant technique is used to engineer additional domains of the antibody into the linker of the scFv (U.S. patent Ser. No. 14/734,953). The native pairing of heavy and light chain immunoglobulins is essentially maintained throughout the process of engineering into full-length expression vector libraries. The vectors are designed in various orientations, for example, two separate promoters drive expression of heavy and light chain immunoglobulins, or one promoter drives expression of both heavy and light chain immunoglobulins, and a translational skip motif is used to separately translate the heavy and light chain immunoglobulins into separate polypeptides. In some embodiments, the expression vectors comprise sequences for site-directed integration into mammalian production cells, for example, CRISPR-Cas9, Flp-In, Cre/Lox, or zinc finger recombination methods. Site-directed integration ensures that each mammalian production cell encodes a single antibody sequence, and decreases variability in expression levels between single production cells.

7.7. Methods of Producing RPPs, e.g., Antibodies

RPPs can be purified from host cells that have been transfected by a gene encoding the antibodies by elution of filtered supernatant of host cell culture fluid using a Heparin HP column, using a salt gradient, or with protein A resin.

Fully human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein. For example, fully human monoclonal antibodies may be obtained from transgenic mice that have been engineered to produce specific human antibodies in response to antigenic challenge. Methods for obtaining fully human antibodies from transgenic mice are described, for example, by Green et al., *Nature Genet.* 7:13, 1994; Lonberg et al., *Nature* 368:856, 1994; Taylor et al., *Int. Immun.* 6:579, 1994; U.S. Pat. No. 5,877,397; Bruggemann et al., 1997 *Curr. Opin. Biotechnol.* 8:455-58; Jakobovits et al., 1995 *Ann. N. Y. Acad. Sci.* 764:525-35. In this technique, elements of the human heavy and light chain locus are introduced into strains of mice derived from embryonic stem cell lines that contain targeted disruptions of the endogenous heavy chain and light chain loci (see also Bruggemann et al., *Curr. Opin. Biotechnol.* 8:455-58 (1997)). For example, human immunoglobulin transgenes may be mini-gene constructs, or transloci on yeast artificial chromosomes, which undergo B-cell-specific DNA rearrangement and hypermutation in the mouse lymphoid tissue. Fully human monoclonal antibodies may be obtained by immunizing the transgenic mice, which may then produce human antibodies specific for the antigen target or targets. Lymphoid cells of the immunized transgenic mice can be used to produce human antibody-secreting hybridomas according to the methods described herein.

Another method for generating human antibodies of the invention includes immortalizing human peripheral blood cells by EBV transformation. See, e.g., U.S. Pat. No. 4,464, 456. Such an immortalized B-cell line (or lymphoblastoid cell line) producing an RPP that specifically binds to target or targets can be identified by immunodetection methods as provided herein, for example, an ELISA, and then isolated by standard cloning techniques. The stability of the lymphoblastoid cell line producing an RPP may be improved by fusing the transformed cell lines with a murine myeloma to produce a mouse-human hybrid cell line according to methods known in the art (see, e.g., Glasky et al., *Hybridoma* 8:377-89 (1989)). Still another method to generate human RPPs is in vitro immunization, which includes priming human splenic B-cells with antigen targets, followed by fusion of primed with a heterohybrid fusion partner. See, e.g., Boerner et al., 1991 *J. Immunol.* 147:86-95.

In certain embodiments, B-cells that are producing an RPP are selected and the light chain and heavy chain variable regions are cloned from the B-cell according to molecular biology techniques known in the art (WO 92/02551; U.S. Pat. No. 5,627,052; Babcook et al., *Proc. Natl. Acad. Sci. USA* 93:7843-48 (1996)) and described herein. B-cells from an immunized animal may be isolated from the spleen, lymph node, or peripheral blood sample by selecting a cell that is producing an antibody that specifically binds to to the antigen target. B-cells may also be isolated from humans, for example, from a peripheral blood sample.

Methods for detecting single B-cells that are producing an antibody with the desired specificity are well known in the art, for example, by plaque formation, fluorescence-activated cell sorting, in vitro stimulation followed by detection of specific antibody, and the like. Methods for selection of specific antibody-producing B-cells include, for example, preparing a single cell suspension of B-cells in soft agar that contains the antigen target. Binding of the specific antibodies produced by the B-cell to the antigen results in the formation of a complex, which may be visible as an immunoprecipitate.

In some embodiments, specific antibody-producing B-cells are selected by using a method that allows identification natively paired antibodies. For example, a method described in Adler et al., A natively paired antibody library yields drug leads with higher sensitivity and specificity than a randomly paired antibody library, MAbs (2018), which is incorporated by reference in its entirety herein, can be employed. The method combines microfluidic technology, molecular genomics, yeast single-chain variable fragment (scFv) display, fluorescence-activated cell sorting (FACS) and deep sequencing. In short, B cells can be isolated from immunized animals and then pooled. The B cells are encapsulated into droplets with oligo-dT beads and a lysis solution, and mRNA-bound beads are purified from the droplets, and then injected into a second emulsion with an OE-RT-PCR amplification mix that generates DNA amplicons that encode scFv with native pairing of heavy and light chain Ig. Libraries of natively paired amplicons are then electroporated into yeast for scFv display. FACS is used to identify high affinity scFv. Finally, deep antibody sequencing can be used to identify all clones in the pre- and post-sort scFv libraries.

After the B-cells producing the desired antibody are selected, the specific antibody genes may be cloned by isolating and amplifying DNA or mRNA according to methods known in the art and described herein.

The methods for obtaining antibodies of the invention can also adopt various phage display technologies known in the art. See, e.g., Winter et al., 1994 *Annu. Rev. Immunol.* 12:433-55; Burton et al., 1994 *Adv. Immunol.* 57:191-280. Human or murine immunoglobulin variable region gene combinatorial libraries may be created in phage vectors that can be screened to select Ig fragments (Fab, Fv, sFv, or multimers thereof) that bind specifically to the RPP or variant or fragment thereof. See, e.g., U.S. Pat. No. 5,223,409; Huse et al., 1989 *Science* 246:1275-81; Sastry et al., *Proc. Natl. Acad. Sci. USA* 86:5728-32 (1989); Alting-Mees et al., *Strategies in Molecular Biology* 3:1-9 (1990); Kang et al., 1991 *Proc. Natl. Acad. Sci. USA* 88:4363-66; Hoogenboom et al., 1992 *J. Molec. Biol.* 227:381-388; Schlebusch et al., 1997 *Hybridoma* 16:47-52 and references cited therein. For example, a library containing a plurality of polynucleotide sequences encoding Ig variable region fragments may be inserted into the genome of a filamentous bacteriophage, such as M13 or a variant thereof, in frame with the sequence encoding a phage coat protein. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426).

In one embodiment, in a hybridoma the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, California), which sells primers for mouse and human variable regions including, among others, primers for $V_{Ha}$, $V_{Hb}$, $V_{Hc}$, $V_{Hd}$, $C_{H1}$, $V_L$ and $C_L$ regions.) These primers may be used to amplify heavy or light chain variable regions, which may then be inserted into vectors such as ImmunoZAP™H or ImmunoZAP™L (Stratagene), respectively. These vectors may then be introduced into *E. coli*, yeast, or mammalian-based systems for expression. Large amounts of a single-chain protein containing a fusion of the $V_H$ and $V_L$ domains may be produced using these methods (see Bird et al., *Science* 242:423-426, 1988).

Once cells producing antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

RPPs of the present invention preferably have activity in the cell-based assays described herein and/or the in vivo assay described herein and/or bind to one or more of the domains described herein. Accordingly, such binding agents can be identified using the assays described herein.

Other antibodies according to the invention may be obtained by conventional immunization and cell fusion procedures as described herein and known in the art.

Molecular evolution of the complementarity determining regions (CDRs) in the center of the antibody binding site also has been used to isolate antibodies with increased affinity, for example, antibodies having increased affinity for c-erbB-2, as described by Schier et al., 1996, *J. Mol. Biol.* 263:551.

Although human, partially human, or humanized antibodies will be suitable for many applications, particularly those involving administration of the antibody to a human subject, other types of antigen binding proteins will be suitable for certain applications. The non-human antibodies of the invention can be, for example, derived from any antibody-producing animal, such as mouse, rat, rabbit, goat, donkey, or non-human primate (such as monkey (e.g., cynomologous or rhesus monkey) or ape (e.g., chimpanzee)). Non-human antibodies of the invention can be used, for example, in in vitro and cell-culture based applications, or any other application where an immune response to the antibody of the invention does not occur, is insignificant, can be prevented, is not a concern, or is desired. In one embodiment, a non-human antibody of the invention is administered to a non-human subject. In another embodiment, the non-human antibody does not elicit an immune response in the non-human subject. In another embodiment, the non-human antibody is from the same species as the non-human subject, e.g., a mouse antibody of the invention is administered to a mouse. An antibody from a particular species can be made by, for example, immunizing an animal of that species with the desired immunogen or using an artificial system for generating antibodies of that species (e.g., a bacterial or phage display-based system for generating antibodies of a particular species), or by converting an antibody from one species into an antibody from another species by replacing, e.g., the constant region of the antibody with a constant region from the other species, or by replacing one or more amino acid residues of the antibody so that it more closely resembles the sequence of an antibody from the other species. In one embodiment, the antibody is a chimeric antibody comprising amino acid sequences derived from antibodies from two or more different species.

Antigen binding proteins may be prepared, and screened for desired properties, by any of a number of conventional techniques. Certain of the techniques involve isolating a nucleic acid encoding a polypeptide chain (or portion thereof) of an RPP of interest, and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example. Furthermore, the antigen binding proteins may be purified from cells that naturally express them (e.g., an antibody can be purified from a hybridoma that produces it), or produced in recombinant expression systems, using any technique known in the art. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, NY, (1988).

Any expression system known in the art can be used to make the recombinant polypeptides of the invention. Expression systems are detailed comprehensively above. In general, host cells are transformed with a recombinant expression vector that comprises DNA encoding a desired polypeptide. Among the host cells that may be employed are prokaryotes, yeast or higher eukaryotic cells. Prokaryotes include gram negative or gram-positive organisms, for example *E. coli* or Bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) as described by McMahan et al., 1991, *EMBO J*. 10: 2821. Appropriate cloning and expression vectors for use with bacterial, fungal, yeast, and mammalian cellular hosts are described by Pouwels et al. (*Cloning Vectors: A Laboratory Manual*, Elsevier, New York, 1985).

Production cell lines for monoclonal antibodies (mAbs) are typically produced by randomly inserting expression constructs into a mammalian production cell genome, for example, a CHO genome (Rita Costa et al., 2010). However, this canonical method produces cell lines with multiple copies of mAb inserted into the CHO genome. If we randomly inserted our polyclonal antibody construct libraries into the CHO genome, many clones would express multiple antibodies, which would result in frequent non-native pairing between heavy and light chain Ig. Additionally, different genome locations have different transcriptional activity levels (Kito et al., 2002), which could result in heterogeneous, inconsistent and/or unstable bioproduction. Thus, in some aspects the current invention provides a CHO cell line with a Flp recombinase recognition target (FRT) landing pad stably engineered into the genome. Such site-directed genome integration cell lines are then used for stable expression of RPPs.

It will be appreciated that an antibody of the present invention may have at least one amino acid substitution, providing that the antibody retains binding specificity. Therefore, modifications to the antibody structures are encompassed within the scope of the invention. These may include amino acid substitutions, which may be conservative or non-conservative that do not destroy the binding capability of an antibody comprising the RPP. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position.

Non-conservative substitutions may involve the exchange of a member of one class of amino acids or amino acid mimetics for a member from another class with different physical properties (e.g. size, polarity, hydrophobicity, charge). Such substituted residues may be introduced into regions of the human antibody that are homologous with non-human antibodies, or into the non-homologous regions of the molecule.

Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three-dimensional structure. In certain embodiments, one skilled in the art may choose not to make radical changes to amino acid residues predicted to be on the surface of the protein, since such residues may be involved in important interactions with other molecules.

A number of scientific publications have been devoted to the prediction of secondary structure. See Moult *J., Curr. Op. in Biotech.,* 7(4):422-427 (1996), Chou et al., *Biochem.,* 13(2):222-245 (1974); Chou et al., *Biochem.,* 113(2):211-222 (1974); Chou et al., *Adv. Enzymol. Relat. Areas Mol. Biol.,* 47:45-148 (1978); Chou et al., *Ann. Rev. Biochem.,* 47:251-276 and Chou et al., *Biophys. J.,* 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., *Nucl. Acid. Res.,* 27(1):244-247 (1999). It has been suggested (Brenner et al., *Curr. Op. Struct. Biol.,* 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., *Curr. Opin. Struct. Biol.,* 7(3):377-87 (1997); Sippl et al., *Structure,* 4(1):15-19 (1996)), "profile analysis" (Bowie et al., *Science,* 253:164-170 (1991); Gribskov et al., *Meth. Enzym.,* 183:146-159 (1990); Gribskov et al., *Proc. Nat. Acad. Sci.,* 84(13):4355-4358 (1987)), and "evolutionary linkage" (See Holm, supra (1999), and Brenner, supra (1997)).

In certain embodiments, variants of antibodies include glycosylation variants wherein the number and/or type of glycosylation site has been altered compared to the amino acid sequences of a parent polypeptide. In certain embodiments, variants comprise a greater or a lesser number of N-linked glycosylation sites than the native protein. An N-linked glycosylation site is characterized by the sequence: Asn-X-Ser or Asn-X-Thr, wherein the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants can be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. *Nature* 354:105 (1991), which are each incorporated herein by reference.

In certain embodiments, antibodies of the invention may be chemically bonded with polymers, lipids, or other moieties.

The binding agents may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically, the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendamistat domains may be used (See e.g., Nygren and Uhlen, 1997, *Curr. Opin. in Struct. Biol.,* 7, 463-469).

It will be appreciated that the antibodies of the invention include the humanized antibodies described herein. Humanized antibodies such as those described herein can be produced using techniques known to those skilled in the art (Zhang, W., et al., *Molecular Immunology.* 42(12):1445-1451, 2005; Hwang W. et al., *Methods.* 36(1):35-42, 2005; Dall'AcquaWF, et al., *Methods* 36(1):43-60, 2005; and Clark, M., *Immunology Today.* 21(8):397-402, 2000).

Where an antibody comprises one or more of CDR1-H, CDR2-H, CDR3-H, CDR1-L, CDR2-L and CDR3-L as described above, it may be obtained by expression from a host cell containing DNA coding for these sequences. A DNA coding for each CDR sequence may be determined on the basis of the amino acid sequence of the CDR and synthesized together with any desired antibody variable region framework and constant region DNA sequences using oligonucleotide synthesis techniques, site-directed mutagenesis and polymerase chain reaction (PCR) techniques as appropriate. DNA coding for variable region frameworks and constant regions is widely available to those skilled in the art from genetic sequences databases such as Gen-Bank®.

Once synthesized, the DNA encoding an antibody of the invention or fragment thereof may be propagated and expressed according to any of a variety of well-known procedures for nucleic acid excision, ligation, transformation, and transfection using any number of known expression vectors. Thus, in certain embodiments expression of an antibody fragment may be preferred in a prokaryotic host, such as *Escherichia coli* (see, e.g., Pluckthun et al., 1989 *Methods Enzymol.* 178:497-515). In certain other embodiments, expression of the antibody or a fragment thereof may be preferred in a eukaryotic host cell, including yeast (e.g., *Saccharomyces cerevisiae, Schizosaccharomyces pombe*, and *Pichia pastoris*), animal cells (including mammalian cells) or plant cells. Examples of suitable animal cells include, but are not limited to, myeloma (such as a mouse NSO line), COS, CHO, or hybridoma cells. Examples of plant cells include tobacco, corn, soybean, and rice cells.

Replicable expression vectors containing DNA encoding an antibody variable and/or constant region may be prepared and used to transform an appropriate cell line, for example, a non-producing myeloma cell line, such as a mouse NSO line or a bacteria, such as *E. coli*, in which production of the antibody will occur. In order to obtain efficient transcription and translation, the DNA sequence in each vector should include appropriate regulatory sequences, particularly a promoter and leader sequence operatively linked to the variable domain sequence. Particular methods for producing antibodies in this way are generally well-known and routinely used. For example, basic molecular biology procedures are described by Maniatis et al. (*Molecular Cloning, A Laboratory Manual, 2nd ed.*, Cold Spring Harbor Laboratory, New York, 1989; see also Maniatis et al, 3rd ed., Cold Spring Harbor Laboratory, New York, (2001)). DNA sequencing can be performed as described in Sanger et al. (*PNAS* 74:5463, (1977)) and the Amersham International plc sequencing handbook, and site directed mutagenesis can be carried out according to methods known in the art (Kramer et al., *Nucleic Acids Res.* 12:9441, (1984); Kunkel *Proc. Natl. Acad. Sci. USA* 82:488-92 (1985); Kunkel et al., *Methods in Enzymol.* 154:367-82 (1987); the Anglian Biotechnology Ltd. handbook). Additionally, numerous publications describe techniques suitable for the preparation of antibodies by manipulation of DNA, creation of expression vectors, and transformation and culture of appropriate cells (Mountain A and Adair, J R in *Biotechnology and Genetic Engineering Reviews* (ed. Tombs, M P, 10, Chapter 1, 1992, Intercept, Andover, UK); "Current Protocols in Molecular Biology", 1999, F. M. Ausubel (ed.), Wiley Interscience, New York).

Where it is desired to improve the affinity of antibodies according to the invention containing one or more of the above-mentioned CDRs can be obtained by a number of affinity maturation protocols including maintaining the CDRs (Yang et al., *J. Mol. Biol.*, 254, 392-403, 1995), chain shuffling (Marks et al., *Bio Technology*, 10, 779-783, 1992), use of mutation strains of *E. coli*. (Low et al., *J. Mol. Biol.*, 250, 350-368, 1996), DNA shuffling (Patten et al., *Curr. Opin. Biotechnol.*, 8, 724-733, 1997), phage display (Thompson et al., *J. Mol. Biol.*, 256, 7-88, 1996) and sexual PCR (Crameri, et al., *Nature*, 391, 288-291, 1998). All of these methods of affinity maturation are discussed by Vaughan et al. (*Nature Biotech.*, 16, 535-539, 1998).

It will be understood by one skilled in the art that some proteins, such as antibodies, may undergo a variety of posttranslational modifications. The type and extent of these modifications often depends on the host cell line used to express the protein as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in Harris, R. J. *Journal of Chromatography* 705:129-134, 1995).

7.8. Pharmaceutical Compositions

Pharmaceutical compositions containing the RPPs of the present invention are also provided. Such compositions comprise a therapeutically or prophylactically effective amount of the polypeptide or protein in a mixture with pharmaceutically acceptable materials, and physiologically acceptable formulation materials.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition.

Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in Remington's Pharmaceutical Sciences, 16th Ed. (1980) and 20th Ed. (2000), Mack Publishing Company, Easton, PA.

Optionally, the composition additionally comprises one or more physiologically active agents, for example, an anti-angiogenic substance, a chemotherapeutic substance (such as capecitabine, 5-fluorouracil, or doxorubicin), an analgesic substance, etc., non-exclusive examples of which are provided herein. In various particular embodiments, the composition comprises one, two, three, four, five, or six physiologically active agents in addition to an RPP.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the polypeptide. For example, suitable compositions may be water for injection, physiological saline solution for parenteral administration.

7.8.1. Content of Pharmaceutically Active Ingredient

In typical embodiments, the active ingredient (i.e., the proteins and polypeptides of the present invention) is present in the pharmaceutical composition at a concentration of at least 0.01 mg/ml, at least 0.1 mg/ml, at least 0.5 mg/ml, or at least 1 mg/ml. In certain embodiments, the active ingredient is present in the pharmaceutical composition at a concentration of at least 1 mg/ml, 2 mg/ml, 3 mg/ml, 4 mg/ml, 5 mg/ml, 10 mg/ml, 15 mg/ml, 20 mg/ml, or 25 mg/ml. In certain embodiments, the active ingredient is present in the pharmaceutical composition at a concentration of at least 30 mg/ml, 35 mg/ml, 40 mg/ml, 45 mg/ml or 50 mg/ml.

7.8.2. Formulation Generally

The pharmaceutical composition can be in any form appropriate for human or veterinary medicine, including a liquid, an oil, an emulsion, a gel, a colloid, an aerosol or a solid.

The pharmaceutical composition can be formulated for administration by any route of administration appropriate for human or veterinary medicine, including enteral and parenteral routes of administration.

In various embodiments, the pharmaceutical composition is formulated for administration by inhalation. In certain of these embodiments, the pharmaceutical composition is formulated for administration by a vaporizer. In certain of these embodiments, the pharmaceutical composition is formulated for administration by a nebulizer. In certain of these embodiments, the pharmaceutical composition is formulated for administration by an aerosolizer.

In various embodiments, the pharmaceutical composition is formulated for oral administration, for buccal administration, or for sublingual administration.

In some embodiments, the pharmaceutical composition is formulated for intravenous, intramuscular, or subcutaneous administration.

In some embodiments, the pharmaceutical composition is formulated for intrathecal or intracerebroventricular administration.

In some embodiments, the pharmaceutical composition is formulated for topical administration.

7.8.3. Pharmacological Compositions Adapted for Injection

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

In various embodiments, the unit dosage form is a vial, ampule, bottle, or pre-filled syringe. In some embodiments, the unit dosage form contains 0.01 mg, 0.1 mg, 0.5 mg, 1 mg, 2.5 mg, 5 mg, 10 mg, 12.5 mg, 25 mg, 50 mg, 75 mg, or 100 mg of the pharmaceutical composition. In some embodiments, the unit dosage form contains 125 mg, 150 mg, 175 mg, or 200 mg of the pharmaceutical composition. In some embodiments, the unit dosage form contains 250 mg of the pharmaceutical composition.

In typical embodiments, the pharmaceutical composition in the unit dosage form is in liquid form. In various embodiments, the unit dosage form contains between 0.1 mL and 50 ml of the pharmaceutical composition. In some embodiments, the unit dosage form contains 1 ml, 2.5 ml, 5 ml, 7.5 ml, 10 ml, 25 ml, or 50 ml of pharmaceutical composition.

In particular embodiments, the unit dosage form is a vial containing 1 ml of the pharmaceutical composition at a concentration of 0.01 mg/ml, 0.1 mg/ml, 0.5 mg/ml, or 1 mg/ml. In some embodiments, the unit dosage form is a vial containing 2 ml of the pharmaceutical composition at a concentration of 0.01 mg/ml, 0.1 mg/ml, 0.5 mg/ml, or 1 mg/ml.

In some embodiments, the pharmaceutical composition in the unit dosage form is in solid form, such as a lyophilate, suitable for solubilization.

Unit dosage form embodiments suitable for subcutaneous, intradermal, or intramuscular administration include pre-loaded syringes, auto-injectors, and autoinject pens, each containing a predetermined amount of the pharmaceutical composition described hereinabove.

In various embodiments, the unit dosage form is a pre-loaded syringe, comprising a syringe and a predetermined amount of the pharmaceutical composition. In certain pre-loaded syringe embodiments, the syringe is adapted for subcutaneous administration. In certain embodiments, the syringe is suitable for self-administration. In particular embodiments, the preloaded syringe is a single use syringe.

In various embodiments, the preloaded syringe contains about 0.1 mL to about 0.5 mL of the pharmaceutical composition. In certain embodiments, the syringe contains about 0.5 mL of the pharmaceutical composition. In specific embodiments, the syringe contains about 1.0 mL of the pharmaceutical composition. In particular embodiments, the syringe contains about 2.0 mL of the pharmaceutical composition.

In certain embodiments, the unit dosage form is an autoinject pen. The autoinject pen comprises an autoinject pen containing a pharmaceutical composition as described herein. In some embodiments, the autoinject pen delivers a predetermined volume of pharmaceutical composition. In other embodiments, the autoinject pen is configured to deliver a volume of pharmaceutical composition set by the user.

In various embodiments, the autoinject pen contains about 0.1 mL to about 5.0 mL of the pharmaceutical composition. In specific embodiments, the autoinject pen contains about 0.5 mL of the pharmaceutical composition. In particular embodiments, the autoinject pen contains about 1.0 mL of the pharmaceutical composition. In other embodiments, the autoinject pen contains about 5.0 mL of the pharmaceutical composition.

7.8.4. Mixtures of Plasma IVIg with Recombinant Hyperimmunes

In some embodiments, a recombinant hyperimmune is spiked into conventional plasma IVIg to increase the anti-pathogen titer of IVIg. In some embodiments, several anti-pathogen recombinant hyperimmunes are spiked into conventional plasma IVIg, for example, hyperimmunes directed against Hib, pneumococcus, influenza A virus, and tetanus are concurrently spiked into plasma IVIg to treat patients with primary immune deficiency. The spike in hyperimmunes increase the titer of antibodies directed against pathogens to which primary immune deficiency patients are particularly susceptible. Any number of spike-ins can be mixed with plasma IVIg to generate increased titers against any number of pathogens.

In some embodiments, the spike-in recombinant hyperimmunes are mixed with plasma IVIg by the pharmacist. In some embodiments, the spike-in recombinant hyperimmunes are mixed with plasma IVIg by the manufacturer.

7.9. Unit Dosage Forms

The pharmaceutical compositions may conveniently be presented in unit dosage form.

The unit dosage form will typically be adapted to one or more specific routes of administration of the pharmaceutical composition.

In various embodiments, the unit dosage form is adapted for administration by inhalation. In certain of these embodiments, the unit dosage form is adapted for administration by a vaporizer. In certain of these embodiments, the unit dosage form is adapted for administration by a nebulizer. In certain of these embodiments, the unit dosage form is adapted for administration by an aerosolizer.

In various embodiments, the unit dosage form is adapted for oral administration, for buccal administration, or for sublingual administration.

In some embodiments, the unit dosage form is adapted for intravenous, intramuscular, or subcutaneous administration.

In some embodiments, the unit dosage form is adapted for intrathecal or intracerebroventricular administration.

In some embodiments, the pharmaceutical composition is formulated for topical administration.

The amount of active ingredient which can be combined with a carrier material to produce a single dosage form will generally be that amount of the compound which produces a therapeutic effect.

7.10. RPP Activity

RPPs, e.g., antibodies according to the invention may have a binding affinity for antigen target of less than or equal to $5 \times 10^{-7}$M, less than or equal to $1 \times 10^{-7}$M, less than or equal to $0.5 \times 10^{-7}$M, less than or equal to $1 \times 10^{-8}$M, less than or equal to $1 \times 10^{-9}$M, less than or equal to $1 \times 10^{-10}$M, less than or equal to $1 \times 10^{-11}$M, or less than or equal to $1 \times 10^{-12}$ M.

The affinity of an RPP, as well as the extent to which an antibody inhibits binding, can be determined by one of ordinary skill in the art using conventional techniques, for example those described by Scatchard et al. (*Ann. N.Y. Acad. Sci.* 51:660-672 (1949)) or by surface plasmon resonance (SPR; BIAcore, Biosensor, Piscataway, NJ). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and disso-ciation phases of the binding reaction. The ratio of these values gives the apparent equilibrium constant (affinity) (see, e.g., Wolff et al., *Cancer Res.* 53:2560-65 (1993)).

7.11. Methods of Treating a Disease Responsive to an RPP

In another aspect, methods are presented for treating a subject having a disease responsive to an RPP. The disease can be cancer, AIDS, Alzheimer's disease or viral or bac-terial infection. In certain aspects, the RPP is used to induce tolerance during transplantation of an organ, tissue, or population of cells from a donor to a host.

The terms "treatment," "treating," and the like are used herein to generally mean obtaining a desired pharmacologic and/or physiologic effect. The effect may be prophylactic, in terms of completely or partially preventing a disease, con-dition, or symptoms thereof, and/or may be therapeutic in terms of a partial or complete cure for a disease or condition and/or adverse effect, such as a symptom, attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms). Improvements in any conditions can be readily assessed according to standard methods and techniques known in the art. The population of subjects treated by the method of the disease includes subjects suffering from the undesirable condition or disease, as well as subjects at risk for development of the condition or disease.

By the term "therapeutically effective dose" or "effective amount" is meant a dose or amount that produces the desired effect for which it is administered. The exact dose or amount will depend on the purpose of the treatment, and will be ascertainable by one skilled in the art using known techniques (see, e.g., Lloyd (1999) The Art, Science and Technology of Pharmaceutical Compounding).

The term "sufficient amount" means an amount sufficient to produce a desired effect.

The term "therapeutically effective amount" is an amount that is effective to ameliorate a symptom of a disease. A therapeutically effective amount can be a "prophylactically effective amount" as prophylaxis can be considered therapy.

The term "ameliorating" refers to any therapeutically beneficial result in the treatment of a disease state, e.g., a neurodegenerative disease state, including prophylaxis, lessening in the severity or progression, remission, or cure thereof.

In vivo and/or in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. Effective doses may be extrapolated from dose-response curves derived from in vitro or animal model test systems.

The actual amount administered, and rate and time-course of administration, will depend on the nature and severity of protein aggregation disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

In some embodiments, the pharmaceutical composition is administered by inhalation, orally, by buccal administration, by sublingual administration, by injection or by topical application.

In some embodiments, the pharmaceutical composition is administered in an amount sufficient to modulate survival of neurons or dopamine release. In some embodiments, the major cannabinoid is administered in an amount less than 1 g, less than 500 mg, less than 100 mg, less than 10 mg per dose.

In some embodiments, the pharmaceutical composition is administered once a day, 2-4 times a day, 2-4 times a week, once a week, or once every two weeks.

8. EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* $3^{rd}$ *Ed.* (Plenum Press) Vols A and B(1992).

8.1. Example 1: Generation of a Library of RPPs with Activity Against Human Thymocytes or T Cells Four libraries of RPPs targeting human thymocytes or T cells, i.e., recombinant human anti-thymocyte globulin (rhATG) were produced. Both in vitro and in vivo studies were used to demonstrate functional similarity between this rhATG and the commercially available rabbit-ATG (Thymoglobulin, Sanofi). The heavy and light chain CDR3 sequences are provided in Table 5 above in RPPs 10-13.

Commercial anti-thymocyte globulin (ATG, (Thymoglobulin, Sanofi)) is useful for inducing transplant tolerance and is manufactured by immunizing New Zealand rabbits with human thymocytes; the blood is harvested from thousands of animals and antibodies are purified from the plasma. The library of RPPs, .i.e., rhATG, disclosed herein combines the efficacy advantages of a polyclonal ATG with the safety advantages of a fully human, recombinant RPP library.

First, transgenic mice carrying inserted human immunoglobulin genes were immunized with human thymocytes or human T cells. Footpad injections were performed on two Trianni Mice twice weekly for three weeks, followed by boosts the following two weeks. One to two million thymocytes were injected into each mouse at each timepoint. Before the final boosts, the serum titer of thymocyte antibodies was assessed by flow cytometry, using a dilution series of each animal's serum, starting at 1:200 and ending at 1:145,000. We observed a strong serum response in both animals, with one animal showing a slightly stronger response. Lymph nodes (popliteal, inguinal, axillary, and mesenteric) were surgically removed after sacrifice. Single cell suspensions for each animal were made by manual disruption followed by passage through a 70 μm filter. Next, we used the EasySep™ Mouse Pan-B Cell Isolation Kit (Stemcell Technologies) negative selection kit to isolate B cells from each sample. The lymph node B cell populations were quantified by counting on a C-Chip hemocytometer (Incyto) and assessed for viability using Trypan blue. The cells were then diluted to 5,000-6,000 cells/mL in phosphate-buffered saline (PBS) with 12% OptiPrep™ Density Gradient Medium (Sigma). This cell mixture was used for microfluidic encapsulation. We ran approximately one million B cells from each of the six animals through our emulsion droplet microfluidics platform.

A DNA library encoding scFv from RNA of single cells, with native heavy-light Ig pairing intact, was generated using the emulsion droplet microfluidics platform or vortex emulsions. The method for generating the DNA library was divided into 1) poly(A)+mRNA capture, 2) multiplexed overlap extension reverse transcriptase polymerase chain reaction (OE-RT-PCR), and 3) nested PCR to remove artifacts and add adapters for deep sequencing or yeast display libraries. The scFv libraries are generated from approximately one million B cells from each animal that achieved a positive titer.

For poly(A)+mRNA capture, a custom designed co-flow emulsion droplet microfluidic chip fabricated from glass (Dolomite) was used. The microfluidic chip has two input channels for fluorocarbon oil (Dolomite), one input channel for the cell suspension mix described above, and one input channel for oligo-dT beads (NEB) at 1.25 mg/ml in cell lysis buffer (20 mM Tris pH 7.5, 0.5 M NaCl, 1 mM ethylene-diaminetetraacetic acid (EDTA), 0.5% Tween-20, and 20 mM dithiothreitol). The input channels are etched to 50 μm by 150 μm for most of the chip's length, narrow to 55 μm at the droplet junction, and were coated with hydrophobic Pico-Glide (Dolomite). Three Mitos P-Pump pressure pumps (Dolomite) were used to pump the liquids through the chip. Droplet size depends on pressure, but typically droplets of ~45 μm diameter were optimally stable. Emulsions were collected into chilled 2 ml microcentrifuge tubes and incubated at 40° C. for 15 minutes for mRNA capture. The beads were extracted from the droplets using Pico-Break (Dolomite). In some embodiments, similar single cell partitioning emulsions are made using a vortex.

For multiplex OE-RT-PCR, glass Telos droplet emulsion microfluidic chips were used (Dolomite). mRNA-bound beads were re-suspended into OE-RT-PCR mix and injected into the microfluidic chips with a mineral oil-based surfactant mix (available commercially from GigaGen) at pressures that generate 27 μm droplets. The OE-RT-PCR mix contains 2× one-step RT-PCR buffer, 2.0 mM MgSO$_4$, SuperScript III reverse transcriptase, and Platinum Taq (Thermo Fisher Scientific), plus a mixture of primers directed against the IgK C region, the IgG C region, and all V regions. The overlap region is a DNA sequence that encodes a Gly-Ser rich scFv linker sequence. The DNA fragments were recovered from the droplets using a droplet breaking solution (available commercially from GigaGen) and then purified using QIAquick PCR Purification Kit (Qiagen). In some embodiments, similar OE-RT-PCR emulsions were made using a vortex.

For nested PCR, the purified OE-RT-PCR product was first run on a 1.7% agarose gel for 80 minutes at 150 V. A band at 1200-1500 base pair (bp) corresponding to the linked product was excised and purified using NucleoSpin Gel and PCR Clean-up Kit (Macherey Nagel). PCR was then performed to add adapters for Illumina sequencing or yeast display; for sequencing, a randomer of seven nucleotides is added to increase base calling accuracy in subsequent next generation sequencing steps. Nested PCR was performed with 2×NEBNext High-Fidelity amplification mix (NEB) with either Illumina adapter containing primers or primers for cloning into the yeast expression vector. The nested PCR product was run on a 1.2% agarose gel for 50 minutes at 150V. A band at 800-1100 bp was excised and purified using NucleoSpin Gel and PCR Clean-up Kit (Macherey Nagel).

To convert the GigaLink™ scFv libraries into full-length CHO expression libraries, nested outer PCR primers were used to add adapters with overhangs for Gibson assembly to the 5' and 3' ends of the scFv library. Then NEBuilder HiFi DNA Assembly Master Mix (NEB, Ipswich, MA, USA) was used to insert the scFv library into a vector containing a single promoter, a secretory leader sequence for light chain Ig and the remainder of the IgG1 constant region, creating a cloned scFv library. This intermediate library was transformed into E. coli, spread onto LB-ampicillin plates, 0.5-1 million colonies were scraped and pooled for a plasmid purification using ZymoPURE II Plasmid Maxiprep Kits (Zymo Research, Irvine, CA, USA). To create the full-length antibody library, a second Gibson assembly was performed by linearizing the product of GA1 with BamHI-HF (NEB, Ipswich, MA, USA) and using it as a vector to insert a synthetic amplicon containing a portion of the light chain Ig constant region, a poly(A) signal for light chain Ig, a promoter for the IgG gene and a secretory leader sequence for the IgG gene. The full-length library was then transformed into E. coli and spread on LB-ampicillin plates Over 0.5 million colonies are scraped and plasmid is purified with a ZymoPURE II Plasmid Maxiprep Kits (Zymo Research) to make the full-length recombinant hyperimmune maxiprep library for transfection.

The adherent Flp-In™-CHO cell line was adapted with a genomically integrated FRT site (Thermo Fisher Scientific, Waltham, MA, USA) to suspension culture. For all steps in the adaptation process, "Ham's F-12" refers to Ham's F-12 (with L-glutamine, Thermo Fisher Scientific, Waltham, MA, USA) plus 10% FBS (Thermo Fisher Scientific, Waltham, MA, USA) and "BalanCD" refers to BalanCD CHO Growth A (Irvine Scientific) with 4 mM Glutamax (Thermo Fisher Scientific, Waltham, MA, USA). To adapt this cell line to suspension, the cells were first passaged into a mixture of 50% Ham's F-12 plus 50% BalanCD in T-flasks. Cells were next passaged into 25% Ham's F-12 plus 75% BalanCD and switched to shaking Erlenmeyer flasks. Cells were then passaged into 10% Ham's F-12, 90% BalanCD+0.2% anti-clumping agent (Irvine Scientific, Santa Ana, CA, USA) and banked for future use.

100 million of the adapted Flp-In CHO cells were transfected per recombinant hyperimmune library using an Amaxa Nucleofector 4D (SG buffer, pulse DU133; Lonza, Basel, Switzerland). These cells were plated into shaking Erlenmeyer flasks and recovered in an incubator at 37° C. and 125 rpm for 48 hours. After 48 hours, the cells were counted to determine viability, cells were seeded at 1 million cells/mL, and selection was started using 600 g/mL Hygromycin-B (Gemini Bio, West Sacramento, CA, USA) in fresh media. Cells were counted and media was changed every 2-3 days during the 7-day selection. The libraries were kept on 600 g/mL Hygromycin-B (Gemini Bio, West Sacramento, CA, USA) during expansion until viability exceeded 95%. When cells were >95% viable and doubling every 24 hours, the cell line was banked for liquid nitrogen storage.

CHO cells stably expressing antibody libraries were grown in media consisting of 90% BalanCD CHO Growth A Medium (Irvine Scientific, Santa Ana, CA), 9% Ham's F-12 (Thermo Fisher Scientific, Waltham, MA, USA), 1% FBS (ThermoFisher Scientific), 4 mM Glutamax (Thermo Fisher Scientific, Waltham, MA, USA), 0.2% anti-clumping agent (Irvine Scientific, Santa Ana, CA, USA). For small-scale production, cells were seeded at $1\times10^6$ cells/mL into 50 mL media in a 250 mL Erlenmeyer flask and grown at 37° C., 5% CO$_2$, 125 rpm. Cells were continually grown under these conditions and supplemented with 7.5 mL CHO Feed 1 (Irvine Scientific, Santa Ana, CA, USA) on days 2, 4 and 7 of the production run. Supernatant was harvested on Day 8 by centrifugation followed by filtration through a 0.22 m 250 mL filter bottle (EMD Millipore, Burlington, MA, USA)

with 1 m pre-filter (EMD Millipore, Burlington, MA, USA). Harvested cell culture fluid (HCCF) was stored at 4° C. until Protein A purification. For large-scale production of the plasma cell recombinant hyperimmune, cells were grown in the same media but with some modifications to the production conditions. A seed train was used to scale the cultures from $2 \times 10^7$ cells to $1.2 \times 10^{10}$ cells at 37° C. Cells were then seeded at $1 \times 10^6$ cells/mL in 2 L in a 5 L flask (in triplicate; Day 0). On Day 2 the temperature was shifted from 37° C. to 33° C. Each flask was fed with 300 mL CHO Feed 1 (Irvine Scientific, Santa Ana, CA, USA) on days 2, 4, 6, 8, 10, and 13 of the culture. Supernatant was harvested on Day 14.

After harvest, HCCF was purified with MabSelect SuRe Protein A resin (GE Life Sciences, Marlborough, MA, USA) using the following buffers: Equilibration, Chase, Wash 2 (25 mM Tris, 150 mM NaCl, pH 7.4), Wash 1 (25 mM Tris, 1 M NaCl, pH 7.4), Elution (20 mM citric acid, pH 3.0), Neutralization (100 mM Tris, pH 8.0 for small scale, 1 M Tris, pH 9.0 for large scale). The column was sanitized before and after use with 0.1 N NaOH. For the large-scale production of the plasma cell recombinant hyperimmune, an additional Wash 3 consisting of 0.5 M arginine, pH 7.4 was used, followed by an additional wash with Wash 2 before elution. The order of purification steps was: Equilibration, Load, Chase, Wash 1, Wash 2, (large scale: Wash 3, Wash 2), Elution, Neutralization (added manually into tubes used for collection of eluate fractions). The recombinant hyperimmunes (RPPs) were concentrated using Vivaspin 20, 30 kDa molecular weight cut off spin concentrators (Sartorius, Gottingen, Germany) and formulated in PBS (small-scale productions) or 0.2 M glycine, pH 4.5 (large scale production), followed by 0.22 m filtration.

ELISA was used to test binding of the rhATG, i.e., anti-T cell and anti-thymocyte RPPs against antigens known to be expressed on the surface of T cells and thymocytes. ELISA showed binding to CD4, CD45, and CD81. Antigens were coated on an ELISA plate at 1 μg/mL. Titration curves were performed starting at 100 ug/mL of each antibody with a 1/3 stepwise dilution to determine the EC50. Because different secondary detection antibodies were used, the EC50 values cannot be directly compared between rabbit-ATG and rhATG. However, it was determined that within each library the antigens that had stronger binding than their respective background. Antibody responses were broadly reactive against many T cell antigens for both rhATG and rabbit-ATG, with both binding very strongly to CD45 and CD5, and binding weaker to CD4, CD11, and CD81 (data not shown).

An in vivo validation study was performed. An in vivo model of GvHD (graft-versus-host-disease) was used to demonstrate the functional efficacy of ATG treatment-induced delay to GvHD. $1 \times 10^7$ human PBMCs from a single donor were engrafted into NSG mice. The study used 6 mice per group with an IV infusion of the drugs tested: rhATG (RPPs), commercial rabbit-ATG, and a vehicle control. Animals were treated (6 mg/kg) at a single timepoint 7 days after engraftment. Additionally, a positive control group (8 mice) received Abatacept, a drug commonly used to prevent GvHD, and this was dosed intraperitoneally (IP) every other day from day 5 to the end of study. Immune cells were measured by flow cytometry for expansion, denoting progression to GvHD, and animals were monitored for weight loss and clinical presentation of GvHD leading to death.

Forty-two days after PBMC engraftment, any animals that were still alive were taken down and a survival analysis was completed for each of the treatment groups. There was no significant delay with rhATG (p=0.2, Mantel-Cox) and only a minor delay to GvHD was observed with rabbit-ATG (p=0.01, Mantel-Cox) (data not shown). Flow cytometry was used to measure engrafted PBMCs before treatment, 2 days after treatment, and 9 days after treatment. rhATG and rabbit-ATG depleted CD45+ cells, as seen 2 days after treatment, leading to a delay in the full engraftment of CD45+ cells, however by day 9 there with no significant difference between any groups (data not shown).

The results demonstrate that the rhATG (library of RPPs) has a similar antigen-specific antibody binding profile as the currently available commercial rabbit-ATG, though some differences were observed. In addition, rhATG also performs similarly to commercial rabbit-ATG in delaying progression to GvHD in mice using different dosing regimens.

8.2. Example 2: Generation of a Library of RPPs with Activity Against *Haemophilus influenzae* Type b (Hib) from Human Donors Both in vitro and in vivo studies pere performed, testing polyclonal antibody pools, (pAb), i.e., libraries of RPPs, with activity against *Haemophilus influenzae* type b (Hib). Tested were anti-Hib pAbs made from four different B cell subtypes collected from donors vaccinated with the Pedvax-HIB conjugate vaccine. The four subtypes tested were CD43+ plasmablasts, CD27+ memory B cells, peripheral CD138+ plasma cells, and pan-B cells (all B cells). All four pAbs were first tested in vitro. The pAb made from CD138+ plasma cells was the most potent in vitro, so this product was then tested relative to IVIG in an in vivo challenge model.

The SEQ ID NOS of the heavy and light chain CDR3 sequences of the RPPs are provided in Table 5 above in RPPs 3-6.

A CRO (BloodCenter Wisconsin, Milwaukee, WI, USA) was used to vaccinate two donors (Donor 1, a 26-year-old Caucasian female, and Donor 2, a 21-year-old Asian male) with PedvaxHIB vaccine (Merck, Kenilworth, NJ, USA). Leukapheresis was performed eight or nine days later to obtain PBMCs. In parallel, plasma was isolated from separate blood draws on the day of leukapheresis and prior to vaccination. ELISA against Hib (Alpha Diagnostics, San Antonio, TX, USA; see methods below) on the plasma samples confirmed a response to the vaccine as compared to plasma from the same donors prior to vaccination. Sample collection protocols were approved by Institutional Review Board (IRB) protocol #PRO00028063 (Medical College of Wisconsin/Froedtert Hospital IRB) to GigaGen. Informed consent was obtained from all participants and samples were shipped to GigaGen de-identified.

To isolate pan-B cells, we used the Human EasySep Pan-B Cell Enrichment Kit (Stemcell #19554, Vancouver, BC, Canada). To isolate CD43+ cells, we used the pan-B cells and positive selection beads for CD43 (Miltenyi #130-091-333, Bergisch Gladbach, Germany). To isolate CD27+ cells, we applied CD27 positive selection beads (Miltenyi #130-051-601, Bergisch Gladbach, Germany) to the negative fraction from the CD43+ selection. For plasma cells, we applied the EasySep Human CD138 Positive Selection Kit (Stemcell #18357, Vancouver, BC, Canada) to PBMCs. After isolation, the antibody-producing cells were cryopreserved using CryoStor® CS10 (Stemcell Technologies, Vancouver, BC, Canada). Immediately prior to generating paired heavy and light chain libraries, cells were thawed, washed in cold DPBS+0.5% BSA, assessed for viability with Trypan blue on a Countess™ cell counter (Thermo Fisher Scientific, Waltham, MA, USA), and then re-suspended in 12%

OptiPrep™ Density Gradient Medium (Sigma, St. Louis, MO, USA) at 5,000-6,000 cells per µl. This cell mixture was used for microfluidic encapslation as described in the next section.

Generation of scFv libraries from antibody-producing cells (Adler et al., *Mabs* 9, 1282-1996, 2017) comprises three steps: (i) poly(A)+ mRNA capture, (ii) multiplexed overlap extension reverse transcriptase polymerase chain reaction (OE-RT-PCR), and (iii) nested PCR to remove artifacts and add adapter sequences for deep sequencing or yeast display libraries.

To convert the GigaLink™ scFv libraries into full-length CHO expression libraries, we first used nested outer PCR primers to add adapters with overhangs for Gibson assembly to the 5' and 3' ends of the scFv library. Then NEBuilder HiFi DNA Assembly Master Mix (NEB, Ipswich, MA, USA) was used to insert the scFv library into a vector containing a single promoter, a secretory leader sequence for light chain Ig and the remainder of the IgG1 constant region, creating a cloned scFv library. This intermediate library was transformed into *E. coli*, spread onto LB-ampicillin plates, 0.5-1 million colonies were scraped and pooled for a plasmid purification using ZymoPURE II Plasmid Maxiprep Kits (Zymo Research, Irvine, CA, USA). To create the full-length antibody library, we performed a second Gibson assembly by linearizing the product of GA1 with BamHI-HF (NEB, Ipswich, MA, USA) and using it as a vector to insert a synthetic amplicon containing a portion of the light chain Ig constant region, a poly(A) signal for light chain Ig, a promoter for the IgG gene and a secretory leader sequence for the IgG gene. The full-length library was then transformed into *E. coli* and spread on LB-ampicillin plates. We typically scrape >0.5 million colonies and purify plasmid with a ZymoPURE II Plasmid Maxiprep Kits (Zymo Research) to make the full-length recombinant hyperimmune maxiprep library for transfection.

We adapted the adherent Flp-In™-CHO cell line with a genomically integrated FRT site (Thermo Fisher Scientific, Waltham, MA, USA) to suspension culture. For all steps in the adaptation process, "Ham's F-12" refers to Ham's F-12 (with L-glutamine, Thermo Fisher Scientific, Waltham, MA, USA) plus 10% FBS (Thermo Fisher Scientific, Waltham, MA, USA) and "BalanCD" refers to BalanCD CHO Growth A (Irvine Scientific) with 4 mM Glutamax (Thermo Fisher Scientific, Waltham, MA, USA). To adapt this cell line to suspension, we first passaged the cells into a mixture of 50% Ham's F-12 plus 50% BalanCD in T-flasks. Cells were next passaged into 25% Ham's F-12 plus 75% BalanCD and switched to shaking Erlenmeyer flasks. Cells were then passaged into 10% Ham's F-12, 90% BalanCD+0.2% anti-clumping agent (Irvine Scientific, Santa Ana, CA, USA) and banked for future use.

100 million of the adapted Flp-In CHO cells were transfected per recombinant hyperimmune library using an Amaxa Nucleofector 4D (SG buffer, pulse DU133; Lonza, Basel, Switzerland). These cells were plated into shaking Erlenmeyer flasks and recovered in an incubator at 37° C. and 125 rpm for 48 hours. After 48 hours, the cells were counted to determine viability, cells were seeded at 1 million cells/mL, and selection was started using 600 g/mL Hygro-mycin-B (Gemini Bio, West Sacramento, CA, USA) in fresh media. Cells were counted and media was changed every 2-3 days during the 7-day selection. The libraries were kept on 600 g/mL Hygromycin-B (Gemini Bio, West Sacramento, CA, USA) during expansion until viability exceeded 95%. When cells were >95% viable and doubling every 24 hours, the cell line was banked for liquid nitrogen storage.

CHO cells stably expressing antibody libraries were grown in media consisting of 90% BalanCD CHO Growth A Medium (Irvine Scientific, Santa Ana, CA), 9% Ham's F-12 (Thermo Fisher Scientific, Waltham, MA, USA), 1% FBS (ThermoFisher Scientific), 4 mM Glutamax (Thermo Fisher Scientific, Waltham, MA, USA), 0.2% anti-clumping agent (Irvine Scientific, Santa Ana, CA, USA). For small-scale production, cells were seeded at $1 \times 10^6$ cells/mL into 50 mL media in a 250 mL Erlenmeyer flask and grown at 37° C., 5% $CO_2$, 125 rpm. Cells were continually grown under these conditions and supplemented with 7.5 mL CHO Feed 1 (Irvine Scientific, Santa Ana, CA, USA) on days 2, 4 and 7 of the production run. Supernatant was harvested on Day 8 by centrifugation followed by filtration through a 0.22 m 250 mL filter bottle (EMD Millipore, Burlington, MA, USA) with 1 m pre-filter (EMD Millipore, Burlington, MA, USA). Harvested cell culture fluid (HCCF) was stored at 4° C. until Protein A purification. For large-scale production of the plasma cell recombinant hyperimmune, cells were grown in the same media but with some modifications to the production conditions. A seed train was used to scale the cultures from $2 \times 10^7$ cells to $1.2 \times 10^{10}$ cells at 37° C. Cells were then seeded at $1 \times 10^6$ cells/mL in 2 L in a 5 L flask (in triplicate; Day 0). On Day 2 the temperature was shifted from 37° C. to 33° C. Each flask was fed with 300 mL CHO Feed 1 (Irvine Scientific, Santa Ana, CA, USA) on days 2, 4, 6, 8, 10, and 13 of the culture. Supernatant was harvested on Day 14.

After harvest, HCCF was purified with MabSelect SuRe Protein A resin (GE Life Sciences, Marlborough, MA, USA) using the following buffers: Equilibration, Chase, Wash 2 (25 mM Tris, 150 mM NaCl, pH 7.4), Wash 1 (25 mM Tris, 1 M NaCl, pH 7.4), Elution (20 mM citric acid, pH 3.0), Neutralization (100 mM Tris, pH 8.0 for small scale, 1 M Tris, pH 9.0 for large scale). The column was sanitized before and after use with 0.1 N NaOH. For the large-scale production of the plasma cell recombinant hyperimmune, we used an additional Wash 3 consisting of 0.5 M arginine, pH 7.4, followed by an additional wash with Wash 2 before elution. The order of purification steps was: Equilibration, Load, Chase, Wash 1, Wash 2, (large scale: Wash 3, Wash 2), Elution, Neutralization (added manually into tubes used for collection of eluate fractions). The recombinant hyperimmunes were concentrated using Vivaspin 20, 30 kDa molecular weight cut off spin concentrators (Sartorius, Gottingen, Germany) and formulated in PBS (small-scale productions) or 0.2 M glycine, pH 4.5 (large scale production), followed by 0.22 m filtration.

Imaged capillary isoelectric focusing (iCIEF) was performed using a Maurice imaging cIEF analyzer (Protein Simple, San Jose, CA, USA). Capillary electrophoresis sodium dodecyl sulfate (CE-SDS) was performed under reducing and non-reducing conditions using LabChip GX II Touch HT (Perkin Elmer, Waltham, MA, USA). Endotoxin levels were measured using Endosafe nexgen-PTS (Charles River, Wilmington, MA, USA).

We observed an HBV RPP yield of 92.2% in our Protein A step. Under non-reducing conditions, we observed a single peak (>99%) at 166.2 kDa with CE-SDS. Under reducing conditions, the RPP showed >99% pure IgG monomer and <1% other proteins, whereas plasma IVIg showed approximately 3.1% unknown protein, suggesting that recombinant hyperimmunes could be produced at higher purity of IgG than plasma IVIg. Analysis of the purified recombinant hyperimmune by iCIEF revealed a broad spectrum of isoelectric species, though plasma IVIg showed a considerably broader range of isoelectric species. We speculate that plasma IVIg has a broader variety of isolectric species because it comprises a broader diversity of antibodies, and also includes different IgG isotypes (the recombinant hyperimmune is only IgG1), as well as IgL. Finally, the endotoxin level was <0.5 endotoxin units (EU)/mg, which is the typical benchmark for recombinant mAb therapeutics.

Deep antibody sequencing libraries were quantified using a quantitative PCR Illumina Library Quantification Kit (KAPA, Wilmington, MA, USA) and diluted to 17.5 pM. Libraries were sequenced on a MiSeq (Illumina, San Diego, CA, USA) using a 500 cycle MiSeq Reagent Kit v2, according to the manufacturer's instructions. To make sequencing libraries, we used tailed-end PCR to add Illumina sequencing adapters to the 5' and 3' ends of the constructs of interest. Then, we obtained forward reads of 340 cycles and reverse reads of 162 cycles. This produced forward and reverse reads that overlap at the CDR3-H and part of the $V_H$-gene, which increased confidence in nucleotide calls. Sequence analysis was performed using our previously reported bioinformatics pipeline (Adler et al., Mabs 9, 1282-1996, 2017). Pearson correlation was performed using the cor function in R version 3.4.2.

Each of four HBV RPPs were derived from 1.12-1.39 million input cells. After the repertoires were subjected to our library generation pipeline, the clonal diversity of the recombinant hyperimmunes were all less than 2,000 antibody clones (range: 880 to 1,659), capturing a considerable fraction of the input antibody diversity. All four recombinant hyperimmunes had a median germline IgHV identity of 93%, suggesting that no cell type yielded antibodies with significantly higher affinity, consistent with prior analysis of Hib-vaccinated individuals (Truck et al., 2015). Clonal diversity was not strongly biased toward the most frequent antibodies in any of the mixtures. The most common antibody was present at a frequency of 3.5% (plasma cell hyperimmune). The pan-B recombinant hyperimmune had the least skewed clonal diversity (the top 20 antibodies were 12.7% of all antibodies), and the plasma cell recombinant hyperimmune had the most skewed clonal diversity (the top 20 antibodies were 26.6% of all antibodies).

We examined the genetic diversity of the four recombinant hyperimmune libraries. An overlap analysis revealed that no more than 11.8% of clones were shared between any given two recombinant hyperimmune libraries. Pearson correlation analysis was not significant between any two pairwise comparisons (p<0.01). All four recombinant hyperimmune libraries contained a variety of IgGV-J gene pairings, including high frequencies of antibodies with IgHV3-23 and IgHJ4 genes, which has been seen elsewhere in anti-Hib repertoires (Silverman & Lucas, 1991; Adderson et al., 1993; Lucas et al., 2003; Truck et al., 2015). Other common IgHV genes included IgHV3-30, IgHV1-69, and IgHV3-7. All libraries also included complementarity-determining region (CDR)3 sequences containing either of the peptides GYGFD or GYGMD, previously observed in anti-Hib repertoires (Lucas et al., 2003; Truck et al., 2015). We conclude that all four libraries contain canonical anti-Hib sequences and similar levels of divergence from germline and genetic diversity. However, the four libraries do comprise distinct antibody mixtures, which may have different functional characteristics.

The Human Anti-Hib-PRP IgG ELISA kit (Alpha Diagnostics #980-100-PHG, San Antonio, TX, USA) was used for anti-Hib ELISA titers. Serial dilutions of antibody preparations were performed in Low NSB (non-specific binding) sample diluent. Quantitative measurements were performed on a plate reader (Molecular Devices, Fremont, CA, USA)

at 450 nm. EC50 values were calculated using SoftMax Pro® (Molecular Devices, Fremont, CA, USA). We also determined the anti-Hib PRP antibody titer for a pool of plasma from both donors before and after vaccination with the Hib active vaccine, as well as IVIg. The plasma cell, pan-B, and plasmablast recombinant hyperimmunes yielded considerably higher Hib-binding titers than IVIg (range: 160× to 2,323×), with the plasma cell hyperimmune yielding the highest titer. The post-vaccination plasma was only 3.7× the anti-Hib titer of IVIg, and no anti-Hib titer was detected in the memory B cell recombinant hyperimmune under the conditions tested. Taken together, these data indicate that our manufacturing process can considerably increase anti-Hib titers simply by selecting appropriate cell types from vaccinated donors.

In vitro neutralization studies were performed at a CRO (ImQuest Frederick, MD, USA). The Haemophilus influenzae type b Eagan strain was obtained from Zeptometrix (#0801679, Buffalo, NY, USA) as a frozen glycerol stock and stored at −80° C. The Haemophilus influenzae strain ATCC 10211 was obtained from the American Type Culture Collection (ATCC, Frederick, MD, USA) as a lyophilized stock and was propagated as recommended by the supplier. Colonies from an overnight incubation on chocolate agar plates were inoculated into growth media (Brain Heart Infusion, or BHI broth, BD BBL 299070, San Jose, CA, USA, with 2% Fildes enrichment, Remel #R45037, San Diego, CA, USA) and allowed to achieve an optical density of 625 nm (OD625) of approximately 0.4. The culture was adjusted to an OD625 of 0.15, which is equivalent to approximately $5\times10^8$ colony forming units (CFU)/mL. The culture was further diluted to $5\times10^4$ CFU/mL in dilution buffer (Hanks Balanced Salt Solution, Gibco, Waltham, MA, USA #14025-092, with 2% Fildes enrichment). The density of the bacterial culture used in the assay was confirmed by plating 50 µL of the $5\times10^3$ and $5\times10^2$ dilutions in duplicate on chocolate agar and enumerating the colonies following incubation at 37° C./5% $CO_2$ for 24 hours.

Test articles were diluted three-fold in dilution buffer, starting at 200 g/mL such that ten total dilutions were evaluated. 10 µL of each dilution of test article were added in duplicate to a 96-well microtiter plate. Eagan or ATCC 10211 bacteria at a concentration of approximately $5\times10^4$ CFU/mL were then added to the plate in a volume of 20 µL, such that the total in-well bacterial density would be $1\times10^4$ CFU/20 µL. Following an incubation of 15 minutes at 37° C./5% $CO_2$, 25 µL of baby rabbit complement (Pel-Freez #31061-1, Rogers, A R, USA) and 25 µL of dilution buffer was added to each well. The plate was incubated at 37° C./5% $CO_2$ for 60 minutes. Following the incubation, 5 µL of each reaction mixture was diluted in 45 µL of dilution buffer and the entire 50 µL was plated on chocolate agar plates. The plates were incubated for approximately 16 hours at 37° C./5% $CO_2$. Following incubation, bacterial colonies were enumerated. The test article concentration that killed >50% of the bacteria is the SBI.

As expected from the ELISA data, the memory B cell recombinant hyperimmune was not able to neutralize either Hib strain at any of the concentrations tested. The plasma cell recombinant hyperimmune again yielded the highest titer, with SBIs of 81 and 243 for the Eagan and ATCC10211 strains, respectively. The pan-B and plasmablast recombinant hyperimmunes were ⅓ah as potent as the plasma cell recombinant hyperimmune. Neutralization was not detected for IVIg at any of the tested concentrations. We conclude that the plasma cell recombinant hyperimmune is the highest potency among the four cell types tested.

All vertebrate experiments were conducted under supervision and approval of either the Institutional Animal Care and Use Committee of Sinclair Research Center, LLC, Missouri (USA) in accordance with the Animal Welfare Act and standards incorporated in the Guide for the Care and Use of Laboratory Animals (National Research Council of the National Academies, Eighth Edition) or the National Committee of Animal Ethics, Denmark, in accordance with the standards of EU Directive 2010/63/EU (permission number: 2014-15-0201-00171).

For acute toxicity, Balb/cJ mice (Charles River, Wilmington, MA, USA) were divided randomly by a CRO (Sinclair Research, Auxvasse, MO, USA) into seven groups of six animals per group. Three of the groups were administered the recombinant hyperimmune at a single dose of 30 mg/kg, 100 mg/kg, or 300 mg/kg. A negative control group was administered a single dose of saline vehicle. The three remaining groups were administered a single dose of plasma IVIg (Gammagard; Grifols, Sant Cugat, Catalonia) at 30 mg/kg, 100 mg/kg, or 300 mg/kg. Test article samples were diluted in 0.2 M Glycine, pH 4.5. Test article administration was performed intravenously through a tail vein. Dose volumes were calculated based on each individual animal's most recent body weight. The mice were then observed twice daily for 8 days for general health, reaction at the site of test article administration, morbidity and mortality, body weight, and gross physical examination (skin, mucous membranes, eyes, ears, nose, and respiration). Animals were euthanized with $CO_2$ gas after 3 days, and terminal serum chemistry was performed, including albumin, globulin, glucose, total protein, blood urea nitrogen, and several other metrics.

We observed no test article-related findings for any of the test groups. We conclude that the no-observed-adverse-effect level (NOAEL) for a single intravenous dose of the plasma cell recombinant hyperimmune is 300 mg/kg. IVIg is typically dosed in immunodeficient patients at around 300 mg/kg for protection against Hib and other pathogens, and the Hib hyperimmune product is thousands-fold more potent, so we conclude that the plasma cell recombinant hyperimmune would have no observable toxicity for a minimally efficacious dose.

For pharmacokinetics, a CRO (Sinclair Research, Auxvasse, MO, USA) administered twenty male Balb/cJ mice (Charles River, Wilmington, MA, USA) one 100 mg/kg intravenous tail vein dose of the plasma cell recombinant hyperimmune. A sparse blood sampling procedure was followed such that no mice received more than two of the scheduled seven PK blood samplings. We then used a sandwich ligand-binding assay (LBA) and Meso Scale Discovery (MSD; Rockville, MD, USA) electrochemiluminescence (ECL) technology to measure serum human IgG. Capture antibody (SouthernBiotech #2049-01, Birmingham, AL, USA) was coated onto 96-well plates (MSD, Rockville, MD, USA). Serum samples were diluted to the minimum required dilution (MRD) of 1:100 in PBS/T containing 1% BSA (PBS/T/BSA). Next, the diluted samples were added to the designated wells. After another wash step, wells were inoculated with PBS/T/BSA containing 1 mg/mL of biotinylated-goat anti-human IgG (SouthernBiotech #2049-08, Birmingham, AL, USA). After incubation, streptavidin-SULFO-TAG was added, followed by 2× read buffer T (MSD, Rockville, MD, USA). ECL units were measured using an MSD QuickPlex SQ 120 instrument. A standard curve was additionally generated for each run using plasma cell-based recombinant hyperimmune. The Discovery Workbench software (MSD, Rockville, MD, USA) was used to fit the data using a four-parameter logistic (4-PL) curve-fit of mean ECL units versus nominal IgG standard values. We removed from further analysis two animals with 1100 ng/mL or lower readings at the 1-hour timepoint, under the assumption that intravenous administration failed. We then used the PKNCA package in R (Denney et al., 2015) to apply non-compartmental analysis to the concentration-time data to estimate maximum observed plasma concentration ($C_{max}$), time of maximum observed plasma concentration ($T_{max}$), and half-life ($t_{1/2}$).

The maximum observed plasma concentration was 12,360 ng/mL ($C_{max}$), observed one hour post-dose ($T_{max}$). The half-life ($t_{1/2}$) of the recombinant hyperimmune was approximately 34.5 hours. Combining these data with the ELISA titer data, we estimate that the maximum anti-Hib trough level was 861 IU/mL for a single 100 mg/kg intravenous dose.

The *Haemophilus influenza* strain ATCC10211 was grown on chocolate agar plates overnight at 35° C. and 5% $CO_2$. Single overnight colonies were resuspended in sterile saline to $1.5 \times 10^8$ CFU/mL. This suspension was diluted in BHI broth with 5% mucin and 2% hemoglobin to approximately $1 \times 10^6$ CFU/mL and further 10-fold diluted to 10 CFU/mL.

Balb/cJ mice (Taconic, Denmark; n=6 per group) were inoculated with single 0.5 mL intraperitoneal doses of $10^4$, $10^5$, or $10^6$ CFU/mL Hib bacteria (strain ATCC10211). Approximately 1 hour before inoculation, mice were treated orally with 45 μL Nurofen (20 mg ibuprofen/mL corresponding to approximately 30 mg/kg) as pain relief. Twenty-four hours prior to inoculation, mice were administered 300 mg/kg recombinant Hib hyperimmune, 300 mg/kg plasma IVIg or saline. One hour after inoculation mice were dosed with 20 mg/kg ciproflaxin antibiotic as positive control treatment. Mice were scored for clinical signs of infection every 2-6th hour and were terminated when severely affected by the infection. After another 72 hours, any living animals were anesthetized with Zoletil mix and blood was collected by axillary cut down. Mice were sacrificed by cervical dislocation, 2 mL sterile saline was injected intraperitoneally, and the abdomen gently massaged before it was opened and fluid sampled with a pipette. Each sample was 10-fold diluted in saline and 20 μL spots were applied on chocolate agar plates. All agar plates were incubated 18-22 hours at 35° C. at ambient air.

The Hib infection was lethal to all but one mouse at all inoculation doses in the vehicle control group. In contrast, only one out of 18 mice was severely affected in the recombinant hyperimmune treatment groups (in the $10^6$ CFU inoculation group). IVIg was much less protective than the recombinant hyperimmune, with 5/6 mice in the $10^5$ CFU and $10^6$ CFU inoculation groups, and 2/6 mice in the $10^4$ CFU inoculation group being severely affected by the infection. Analysis of bacterial loads in blood demonstrated that the recombinant hyperimmune eliminated Hib from the bloodstream of all animals, whereas IVIg treatment resulted in significantly lower bacterial loads than the vehicle control in only one of the inoculation groups and no significant reduction in two inoculation groups (Dunnett's multiple comparisons test, p<0.05). In peritoneal lavage, the recombinant hyperimmune again significantly reduced the bacterial loads compared to the vehicle control group (Dunnett's multiple comparisons test, p<0.05). However, whereas Hib bacteria were not detectable in the peritoneal lavage of surviving animals treated with ciproflaxin, Hib bacteria were detectable in the peritoneal lavage of 6/17 surviving animals treated with recombinant hyperimmune (range: 23-77 CFU/ mL). This suggests differences in the efficacy of the recombinant hyperimmune between the peritoneum and blood, perhaps due to bioavailability of drug or complement in the peritoneum.

In some embodiments, the Hib hyperimmune is spiked into conventional plasma IVIg to increase the anti-Hib titer of IVIg. In some embodiments, several anti-pathogen hyperimmunes are spiked into conventional plasma IVIg, for example, hyperimmunes directed against Hib, pneumococcus, influenza A virus, and tetanus are spiked into plasma IVIg to treat patients with primary immune deficiency. The spike in hyperimmunes increase the titer of antibodies directed against pathogens to which primary immune deficiency patients are particularly susceptible. Any number of spike-ins can be mixed with plasma IVIg to generate increased titers against any number of pathogens.

Using a series of in vitro and in vivo experiments, the following was determined. For Hib, plasma cells following vaccination produce the most potent RPP. The plasma cell Hib RPP was >2,300× more potent (by ELISA) than plasma IVIG. The plasma cell Hib RPP strongly protected against Hib infection in an in vivo challenge model. Use of plasmablasts and pan-B cells also led to a potent RPP in vitro, albeit less potent than plasma cells. For this antigen, the RPP made from memory B cells had undetectable levels of potency in the in vitro assays.

8.3. Example 3: Generation of a Library of RPPs with Activity Against *Streptococcus pneumoniae* Capsular Polysaccharides

*Streptococcus pneumoniae* causes pneumococcal pneumonia. A recombinant polyclonal antibody (pAb), i.e., library of RPPs, with activity towards *Streptococcus pneumoniae* was generated, "GG-Pnc." GG-Pnc tested in vitro. The results demonstrate the in vitro functional efficacy and potency of GG-Pnc with activity against *Streptococcus pneumoniae* capsular polysaccharides. The library was analyzed by bulk pneumococcal polysaccharide ELISA, serotype-specific ELISA, and serotype-specific opsonophagocytic assays.

The SEQ ID NOS of the heavy and light chain CDR3 sequences of the GG-Pnc are provided in Table 5 above (RPP1).

Using the recombinant techniques described in examples 1 and 2, GG-Pnc, i.e., a library of RPPs was prepared. This library was prepared from three donors vaccinated with the Pneumovax-23 vaccine. Pneumovax-23 consists of capsular polysaccharides from 23 pneumococcal serotypes. All three donors showed an increase in titer against pneumococcal capsular polysaccharides after vaccination, as measured by ELISA. The rpAb was made from a mixture of all B cell subtypes isolated from the donors.

The Alpha Diagnostics ELISA measures bulk polysaccharide-specific antibody responses to the 23 pneumococcal polysaccharides found in the Pneumovax-23 vaccine and was used to measure an EC50 of the RPP library. An 8-step, 3-fold dilution series was performed, and a 4-point logistic analysis was performed to calculate the EC50. The RPP library GG-Pnc was ~100 times more potent than IVIG.

A serotype multiplex ELISA was performed to assess antibody diversity of the GG-Pnc RPP library compared to IVIG. Twenty pneumococcal serotypes were measured by ELISA. Using an international standard for pneumococcal-specific responses, antibody-specific responses in GG-Pnc and IVIG (Gamunex) were measured. GG-Pnc had a similar or higher concentration than IVIG against all serotypes except for serotype 6A.

Serotype-specific opsonophagocytosis assays were performed to assess antibody-induced killing function. Fourteen pneumococcal serotypes were measured by opsonophagocytosis responses using GG-Pnc and IVIG (Gamunex). Consistent with the multiplex-ELISA, GG-Pnc was similar to or more effective than IVIG for all serotypes except for 6A.

A serotype 2-specific ELISA was performed to determine the ability of GG-Pnc to bind to this serotype, since it was not included in the prior analysis, but it is an available option for an in vivo mouse model. An 8-step, 3-fold dilution series was performed, and a 4-point logistic analysis was used to calculate the EC50; only GG-Pnc had a value since IVIG had minimal binding to serotype 2, even at very high concentrations.

The GG-Pnc RPP library strongly bound a diverse set of pneumococcal serotypes and was able to neutralize all serotypes tested based on in vitro opsonophagocytosis assays. GG-Pnc was similar to or more potent than IVIG for all but one serotype (for both binding and killing), with no serotype-specific enrichment procedures performed and using all B cells isolated from the vaccinated donors. GG-Pnc also strongly bound to serotype 2.

8.4. Example 4: Generation of a Library of RPPs with Activity Against Influenza A Antigen A library of RPPs with activity towards Influenza A antigen (RPP1) was generated using the recombinant methods described herein.

The SEQ ID NOS of the heavy and light chain CDR3 sequences of RPP1 are provided in Table 5 above (RPP1).

8.5. Example 5: Generation of a Library of RPPs with Activity Against Hepatitis B Virus Antigen (Engerix, GSK)

Two libraries of RPPs with activity against Hepatitis B virus antigen (RPP8 and RPP9) was generated using the recombinant methods described herein.

The SEQ ID NOS of the heavy and light chain CDR3 sequences of RPP9 and RPP9 are provided in Table 5 above (RPP1).

9. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

10. EQUIVALENTS

Whereas various specific embodiments have been illustrated and described, the above specification is not restrictive. It will be appreciated that various changes can be made without departing from the spirit and scope of the invention(s). Many variations will become apparent to those skilled in the art upon review of this specification.

SEQUENCE LISTING

The patent contains a lengthy sequence listing. A copy of the sequence listing is available in electronic form from the USPTO web site (https://seqdata.uspto.gov/docdetail?docId=US12590386B2). An electronic copy of the sequence listing will also be available from the USPTO upon request and payment of the fee set forth in 37 CFR 1.19(b)(3).

The invention claimed is:

1. A pharmaceutical composition comprising a library of recombinant polyclonal proteins (RPPs), wherein the library comprises at least 100 RPPs specifically binding to an antigen and has been generated by the process of:
   a. isolating single cells from a spleen, lymph node, or peripheral blood sample from a donor exposed to the antigen, wherein the single cells are CD43$^+$ plasmablasts, CD27$^+$ memory B cells, or peripheral CD138$^+$ plasma cells;
   b. amplifying polynucleotides, wherein each of the polynucleotides encodes a cognate pair of heavy chain and light chain variable regions from one of the single cells by overlap extension reverse transcriptase polymerase chain reaction (OE-RT-PCR);
   c. cloning the polynucleotides obtained from the amplification into an expression vector, thereby obtaining the constructs encoding antibody fragments;
   d. generating antibody expression constructs using the constructs or a subset of the constructs, wherein each of the antibody expression constructs encodes a light chain variable region, a kappa or lambda-type light chain constant region, a heavy chain variable region, and a heavy chain constant region,
   e. introducing the antibody expression constructs into a cell line, and
   f. expressing antibodies from the antibody expression constructs in the cell line, thereby obtaining the at least 100 recombinant polyclonal proteins (RPPs); wherein each of the RPP is an antibody comprising a cognate pair of heavy chain and light chain variable regions from a single cell out of the sample.

2. The pharmaceutical composition of claim 1, wherein the process further comprises the step of obtaining the subset of the constructs after step c. by expressing the antibody fragments from the constructs and enriching the subset of the constructs based on the binding activities of the antibody fragments against the antigen.

3. The pharmaceutical composition of claim 1,
   a. wherein the antigen is an antigen of *Haemophilus influenzae* type b (Hib), or
   b. wherein the antigen is an antigen of *Streptococcus pneumoniae*, or
   c. wherein the antigen is an antigen of Influenza A, or
   d. wherein the antigen is an antigen of Hepatitis B virus, or
   e. wherein the antigen is an antigen of human thymocyte or human T cells, or
   f. wherein the antigen is selected from CD4, CD45, and CD81.

4. The pharmaceutical composition of claim 1, wherein the library comprises at least 1000 or at least 10,000 RPPs.

5. The pharmaceutical composition of claim 1, wherein the single cells from the sample are CD138+ plasma cells.

6. The pharmaceutical composition of claim 1, wherein each of the RPP is an IgG1 antibody.

* * * * *